United States Patent [19]

Smithwick, Jr. et al.

[11] 4,322,342
[45] Mar. 30, 1982

[54] ANALGESIC COMPOUNDS

[75] Inventors: Edward L. Smithwick, Jr.; Robert C. A. Frederickson, both of Indianapolis; Robert T. Shuman, Greenwood, all of Ind.

[73] Assignee: Eli Lilly and Company, Indianapolis, Ind.

[21] Appl. No.: 202,513

[22] Filed: Oct. 31, 1980

Related U.S. Application Data

[60] Division of Ser. No. 807,849, Jun. 20, 1977, Pat. No. 4,259,234, which is a continuation-in-part of Ser. No. 726,724, Sep. 27, 1976, abandoned.

[51] Int. Cl.³ .......................................... C07C 103/52
[52] U.S. Cl. ............................................. 260/112.5 E
[58] Field of Search ................................ 260/112.5 E

[56] References Cited

U.S. PATENT DOCUMENTS 4,178,371 12/1979 Morgan ..................... 260/112.5 E
4,259,234 3/1981 Smithwick, Jr. et al. ... 260/112.5 R

*Primary Examiner*—Delbert R. Phillips
*Attorney, Agent, or Firm*—William C. Martens; Arthur R. Whale

[57] ABSTRACT

Compounds of the formula

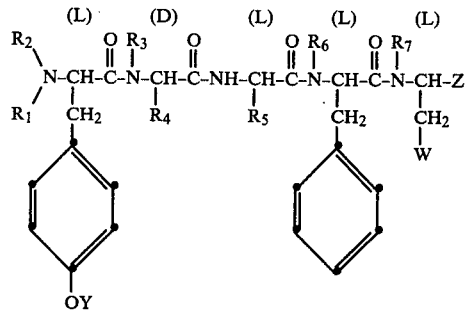

and pharmaceutically acceptable non-toxic acid addition salts thereof, in which:

L and D, when applicable, define the chirality;
$R_1$ is hydrogen, $C_1$-$C_3$ primary alkyl, or allyl;
$R_2$ is hydrogen or $C_1$-$C_3$ primary alkyl, subject to the limitation that when $R_1$ is allyl, $R_2$ is hydrogen;
$R_3$ is hydrogen or $C_1$-$C_3$ primary alkyl;
$R_4$ is $C_1$-$C_4$ primary or secondary alkyl;
$R_5$ is hydrogen or $C_1$-$C_4$ primary or secondary alkyl;
$R_6$ is hydrogen or $C_1$-$C_3$ primary alkyl;
$R_7$ is hydrogen or $C_1$-$C_3$ primary alkyl;
Y is hydrogen or acetyl;
Z is hydrogen or

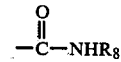

in which $R_8$ is $C_1$-$C_3$ alkyl or hydrogen; and W is isopropyl, —$VR_9$, or —$CH_2$—X—$CH_3$, in which V is O or S, $R_9$ is $C_1$-$C_4$ alkyl or aralkyl, and X is O, S, or —$CH_2$—, subject to the limitation that, when W is isopropyl, $R_7$ is $C_1$-$C_3$ primary alkyl; are useful analgesic agents.

67 Claims, No Drawings

ANALGESIC COMPOUNDS

CROSS REFERENCE

This is a division of application Ser. No. 807,849, filed June 20, 1977, now U.S. Pat. No. 4,259,234, which is a continuation-in-part of application Ser. No. 726,724, filed Sept. 27, 1976, and now abandoned.

BACKGROUND OF THE INVENTION

This invention relates to a novel class of compounds which exhibit analgesic activity upon parenteral administration.

Recently, endogenous substances having morphine-like properties have been extracted from mammalian brain or csf. These substances, named enkephalin, have been identified by Hughes et al., *Nature,* 258, 577 (1975) as pentapeptides having the following sequences:

H-Tyr-Gly-Gly-Phe-Met-OH

H-Tyr-Gly-Gly-Phe-Leu-OH.

These compounds are referred to as methionine-enkephalin and leucine-enkephalin, respectively.

Although these compounds have been shown to exhibit analgesic activity in mice upon administration intracerebroventricularly [Buscher et al., *Nature,* 261, 423 (1976)], they are practically devoid of any useful analgesic activity when administered parenterally.

A novel class of compounds has now been discovered. These compounds exhibit significant and demonstrable analgesic activity when administered systemically. It is to this class of compounds that this invention is directed.

SUMMARY OF THE INVENTION

Thus, this invention relates to a class of compounds having the formula

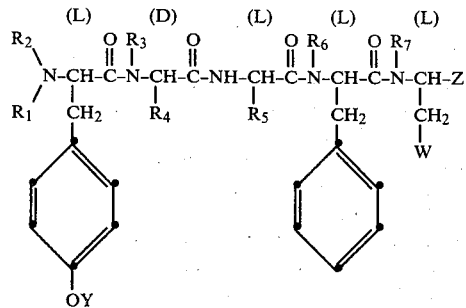

and pharmaceutically acceptable non-toxic acid addition salts thereof, in which:

L and D, when applicable, define the chirality;
$R_1$ is hydrogen, $C_1-C_3$ primary alkyl, or allyl;
$R_2$ is hydrogen or $C_1-C_3$ primary alkyl, subject to the limitation that when $R_1$ is allyl, $R_2$ is hydrogen;
$R_3$ is hydrogen or $C_1-C_3$ primary alkyl;
$R_4$ is $C_1-C_4$ primary or secondary alkyl;
$R_5$ is hydrogen or $C_1-C_4$ primary or secondary alkyl;
$R_6$ is hydrogen or $C_1-C_3$ primary alkyl;
$R_7$ is hydrogen or $C_1-C_3$ primary alkyl;
Y is hydrogen or acetyl;
Z is hydrogen or

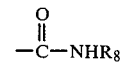

in which $R_8$ is $C_1-C_3$ alkyl or hydrogen; and W is isopropyl, $-VR_9$, or $-CH_2-X-CH_3$, in which V is O or S, $R_9$ is $C_1-C_4$ alkyl or aralkyl, and X is O, S, or $-CH_2-$, subject to the limitation that, when W is isopropyl, $R_7$ is $C_1-C_3$ primary alkyl.

A preferred class of compounds is that class in which W is $-CH_2-X-CH_3$, and, of this class, those compounds in which X is sulfur.

DETAILED DESCRIPTION OF THE INVENTION

As indicated above, the compounds of this invention have the following structure:

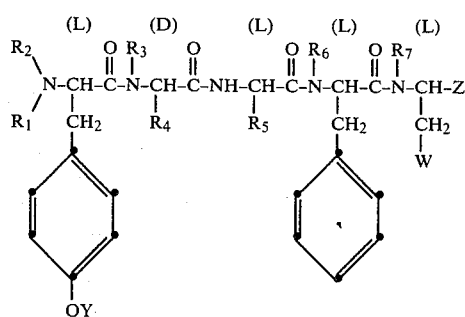

Also included are the pharmaceutically acceptable non-toxic acid addition salts of these compounds.

Pharmaceutically acceptable non-toxic acid addition salts include the organic and inorganic acid addition salts, for example, those prepared from acids such as hydrochloric, sulfuric, sulfonic, tartaric, fumaric, hydrobromic, glycolic, citric, maleic, phosphoric, succinic, acetic, nitric, benzoic, ascorbic, p-toluenesulfonic, benzenesulfonic, naphthalenesulfonic, propionic, and the like. Preferably, the acid addition salts are those prepared from hydrochloric acid, acetic acid, or succinic acid. Any of the above salts are prepared by conventional methods.

As will be noted from the definition of the various substituents which appear in the above structure, the compounds which are defined by this structure are unsubstituted or N-substituted amides of pentapeptides or N-substituted or N,N-disubstituted amides of tetrapeptides. The stereoconfiguration of the compounds of this invention is an essential feature thereof. For the sake of convenience, the amino acid residues of the pentapeptides of this invention are numbered sequentially beginning with the residue at the terminal amino function. The chirality of the amino acid residues, reading from Position 1 through Position 5, thus is L, D, L, L, and L. When the compounds which are defined by this invention constitute a tetrapeptide, the above chiral sequence pertains with the exception that the amino acid residue which originally represented Position 5 is omitted. Furthermore, it is to be noted that the residue in Position 3 is defined to include a glycine moiety. In those cases, of course, no chirality as to this residue exists. It is important only to recognize that, when Position 3 does define an amino acid residue having chirality, that chirality must be L.

The group $R_8$ as used herein is defined to include the group "$C_1$–$C_3$ alkyl". By the term "$C_1$–$C_3$ alkyl" is intended methyl, ethyl, n-propyl and isopropyl.

The groups $R_1$, $R_2$, $R_3$, $R_6$, and $R_7$ as used herein are defined to include the group "$C_1$–$C_3$ primary alkyl". By the term "$C_1$–$C_3$ primary alkyl" is intended methyl, ethyl, and n-propyl.

The groups $R_4$ and $R_5$ appearing in the above structural formula are defined to include the group "$C_1$–$C_4$ primary or secondary alkyl". By the term "$C_1$–$C_4$ primary or secondary alkyl" is meant methyl, ethyl, n-propyl, isopropyl, n-butyl, isobutyl, and sec-butyl.

The group $R_9$ as used herein is defined to include the groups "$C_1$–$C_4$ alkyl" and "aralkyl". By the term "$C_1$–$C_4$ alkyl" is meant methyl, ethyl, n-propyl, isopropyl, n-butyl, isobutyl, sec-butyl, and t-butyl. Preferably, $R_9$, when it is $C_1$–$C_4$ alkyl, is ethyl. By the term "aralkyl" is meant unsubstituted and substituted aralkyls and preferably is directed to those aralkyl groups having from about 7 to about 10 carbon atoms. More preferably, the aralkyl group is benzyl or substituted benzyl. Typical substituents include halo, such as fluoro, chloro, or bromo; $C_1$–$C_3$ alkoxy, such methoxy, ethoxy, or propoxy; trifluoromethyl; $C_1$–$C_3$ alkyl; or $C_1$–$C_3$ alkylthio, such as methylthio, ethylthio, and the like. Preferably, the substituent, when one is present, is located in the para position. A highly preferred substituent is methoxy, and highly preferred aralkyl group is p-methoxybenzyl.

With respect to the particular position residues of the tetrapeptides and pentapeptides of this invention, the following considerations prevail:

(A) Position 1.

This position represents the amino-terminal portion of the peptide. The residue is that which results from L-tyrosine or L-(O-acetyl)tyrosine. In either instance, the residue can be N-unsubstituted, in which case both $R_1$ and $R_2$ are hydrogen. It can be substituted by an allyl group, in which case $R_1$ is allyl. Moreover, the residue can be substituted by one or two $C_1$–$C_3$ primary alkyl groups, in which case $R_1$ and/or $R_2$ is $C_1$–$C_3$ primary alkyl. Specific illustrations of $C_1$–$C_3$ primary alkyl substitution include N-methyl-, N-ethyl-, N-n-propyl-, N,N-dimethyl, N,N-diethyl, N,N-di-n-propyl, N-methyl-N-ethyl, N-methyl-N-n-propyl, N-ethyl-N-n-propyl, and the like. Preferably, the tyrosyl or O-acetyltyrosyl residue which is present in Position 1 of the peptide of this invention is N-unsubstituted. Furthermore, it is preferred that the residue is tyrosyl.

(B) Position 2.

The amino acid residue which is present in the second position of the peptide of this invention must be the D stereoisomer and is any of several amino acid residues. These include residues derived from D-alanine (Ala) ($R_4$ is methyl), D-α-aminobutyric acid (Abu) ($R_4$ is ethyl), D-norvaline (Nva) ($R_4$ is n-propyl), D-valine (Val) ($R_4$ is isopropyl), D-norleucine (Nle) ($R_4$ is n-butyl), D-leucine (Leu) ($R_4$ is isobutyl), and D-isoleucine (Ile) ($R_4$ is sec-butyl). Preferably, the residue is that derived from D-alanine. In any of these amino acid residues, the group $R_3$ present on the nitrogen representing the amino group of the original amino acid is either hydrogen or a $C_1$–$C_3$ primary alkyl. In the latter instance, the amino acid residue is N-substituted. Such N-substituted amino acid residues are represented by N-methyl, N-ethyl, and N-n-propyl. Preferably, the amino acid in Position 2 is N-unsubstituted, i.e., $R_3$ is hydrogen.

(C) Position 3.

The amino acid residue present in this position is that derived from glycine (Gly) or from any of a group of L amino acids. The amino acids include the following: L-alanine, L-(αamino)butyric acid, L-norvaline, L-valine, L-norleucine, L-leucine, and L-isoleucine. Preferably, the residue in this position of the peptide is that derived from glycine.

(D) Position 4.

The amino acid residue present in this position is that derived from L-phenylalanine (Phe). The residue can be either unsubstituted or substituted at the amino nitrogen ($R_6$). In the event that the residue is N-substituted, it is N-methyl, N-ethyl, or N-n-propyl. Preferably, the residue is N-unsubstituted ($R_6$ is hydrogen).

(E) Position 5.

(1) Pentapeptide.

With respect to those compounds of this invention which define a pentapeptide

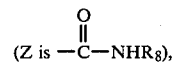

$$(Z \text{ is } -\overset{\overset{\displaystyle O}{\|}}{C}-NHR_8),$$

the amino acid residue in Position 5 of the pentapeptide is the residue of an amide of L-methionine (Met) (W is —$CH_2SCH_3$), L-norleucine (Nle) (W is —$CH_2CH_2CH_3$), L-(O-methyl)homoserine [Hse(Me)] (W is —$CH_2OCH_3$), L-leucine (Leu) [W is —$CH(CH_3(CH_3))_2$], L-(O-alkyl or aralkyl)serine [Ser(Alk) or Ser(Aralk)] (W is $OR_9$), or L-(S-alkyl or aralkyl)cysteine [Cys(Alk) or Cys(Aralk)] (W is $SR_9$). Preferably, the amino acid residue in Position 5 is the residue of an amide of L-methionine or an amide of L-leucine. In those instances in which the residue in Position 5 is O-substituted serine or S-substituted cysteine, it is preferred, when the substituent is a $C_1$–$C_4$ alkyl, that it is ethyl and, when it is aralkyl, that it is p-methoxybenzyl.

The residue of this terminal amino acid, when it is other than L-leucine, is either unsubstituted or substituted at its amino nitrogen. When the terminal amino acid residue is L-leucine, it is substituted at its amino nitrogen. In those instances in which a substituent is present, the substituent is a $C_1$–$C_3$ primary alkyl group. The represented substituents are N-methyl, N-ethyl, and N-n-propyl. Preferably, the amino nitrogen is substituted, i.e., $R_7$ is $C_1$–$C_3$ primary alkyl. More preferably, the $C_1$–$C_3$ primary alkyl group is methyl.

In addition, since the amino acid in Position 5 of the pentapeptide represents the terminal carboxyl amino acid, it, in accordance with this invention, is present as an amide. Preferably, the amide is N-unsubstituted, i.e., $R_8$ is hydrogen. However, the amide group can be N-monosubstituted, the substituent being a $C_1$–$C_3$ alkyl group. In those instances, the terminal amide group is N-methyl, N-ethyl, N-n-propyl, or N-isopropyl.

(2) Tetrapeptide.

It also is possible in accordance with this invention in effect to eliminate the Position 5 residue, making the L-phenylalanyl Position 4 residue the carboxyl terminal amino acid. In those instances, the resulting terminal L-phenylalanyl is present as an amide which is either N-monosubstituted or N,N-disubstituted at the amide function. In those instances in which the group is N-monosubstituted, the particular substituent is N-(3-methoxy)propyl; N-(3-methylthio)propyl; N-n-pentyl; N-(3-methyl)butyl; N-(2-alkoxy)ethyl, such as N-(2- methoxy)ethyl, N-(2-ethoxy)ethyl, N-(2-n-propoxy)ethyl, and the like; N-(2-aralkoxy)ethyl, such as N-(2-benzyloxy)ethyl, N-(2-p-methoxybenzyloxy)ethyl, N-(2-m-chlorobenzyloxy)ethyl, N-(2-o-trifluoromethylbenzyloxy)ethyl, N-(2-m-ethoxybenzyloxy)ethyl, and the like; N-(2-alkylthio)ethyl, such as N-(2-methylthio)ethyl, N-(2-ethylthio)ethyl, N-(2-isopropylthio)ethyl, N-(2-n-butylthio)ethyl, and the like; or N-(2-aralkylthio)ethyl, such as N-(2-benzylthio)ethyl, N-(2p-methoxybenzylthio)ethyl, N-(2-o-bromobenzylthio)ethyl, N-(2-p-ethylthiobenzylthio)ethyl, N-(2-p-methylbenzylthio)ethyl, and the like. In those instances in which the terminal amide group is N,N-disubstituted, the substituents are one of any of the above classes and a $C_1$–$C_3$ primary alkyl group. The groups thereby represented include, for example, N-methyl-N-(3-methoxy)propyl, N-methyl-N-(3-methylthio)propyl, N-methyl-N-n-pentyl, N-ethyl-N-(3-methylthio)propyl, N-n-propyl-N-n-pentyl, N-ethyl-N-(3-methoxy)propyl, N-n-propyl-N-(3-methylthio)propyl, N-methyl-N-(3-methyl)butyl, N-ethyl-N-(3-methyl)butyl, N-methyl-N-(2-ethoxy)ethyl, N-methyl-N-(2-p-methoxybenzyloxy)ethyl, N-ethyl-N-(2-p-methoxybenzyloxy)ethyl, N-methyl-N-(2-ethylthio)ethyl, N-n-propyl-N-(2-methylthio)ethyl, N-methyl-N-(2-p-methoxybenzylthio)ethyl, N-ethyl-N-(2-m-fluorobenzylthio)ethyl and the like.

In this specification, the following abbreviations, most of which are well known and are commonly used in the art, are employed:

Abu—αaminobutyric acid
Ala—alanine
Cys—cysteine
Gly—glycine
Hse—homoserine
Ile—isoleucine
Leu—Leucine
Met—methionine
Nle—norleucine
Nva—norvaline
Phe—phenylalanine
Ser—serine
Tyr—tyrosine
Val—valine
Ac—acetyl
Me—methyl
Et—ethyl
Ip—isopropyl
Pr—n-propyl
Bu—n-butyl
i-Bu—isobutyl
t-Bu—t-butyl
s-Bu—sec-butyl
BOC—t-butyloxycarbonyl
Bzl—benzyl
DCC—N,N'-dicyclohexylcarbodiimide
HBT—1-hydroxybenzotriazole
DMF—N,N-dimethylformamide
TFA—trifluoroacetic acid
THF—tetrahydrofuran
DEAE—diethylaminoethyl Examples of typical compounds of this invention include the following:

H-L-Tyr-D-Ala-Gly-L-Phe-L-Met-NH$_2$;
H-L-Tyr-D-Ala-Gly-L-Phe-L-(N-Me)Met-NH$_2$;
H-L-Tyr-D-Abu-Gly-L-Phe-L-Met-NH$_2$;
H-L-Tyr-D-Abu-Gly-L-Phe-L-(N-Me)Met-NH$_2$;
H-L-Tyr-D-Nva-Gly-L-Phe-L-(N-Me)Met-NH$_2$;
H-L-Tyr-D-Nva-Gly-L-Phe-L-Met-NH$_2$;
H-L-Tyr-D-Val-Gly-L-Phe-L-(N-Me)Met-NH$_2$;
H-L-Tyr-D-Val-Gly-L-Phe-L-Met-NH$_2$;
H-L-Tyr-D-Nle-Gly-L-Phe-L-Met-NH$_2$;
H-L-Tyr-D-Nle-Gly-L-Phe-L-(N-Et)Met-NH$_2$;
H-L-Tyr-D-Leu-Gly-L-Phe-L-Met-NH$_2$;
H-L-Tyr-D-Leu-Gly-L-Phe-L-(N-Pr)Met-NH$_2$;
H-L-Tyr-D-Ile-Gly-L-Phe-L-Met-NH$_2$;
H-L-Tyr-D-Ile-Gly-L-Phe-L-(N-Pr)Met-N$_2$;
H-L-Tyr-D-Ala-Gly-L-Phe-L-(N-Et)Met-NH$_2$;
H-L-Tyr-D-Ala-Gly-L-Phe-L-(N-Pr)Met-NH$_2$;
H-L-Tyr-D-Ala-D-Ala-L-Phe-L-(N-Pr)Met-NH$_2$;
H-L-Tyr-D-Ala-L-Ala-L-Phe-L-Met-NH$_2$;
H-L-Tyr-D-Ala-L-Ala-L-Phe-L-(N-Me)Met-NH$_2$;
H-L-Tyr-D-Ala-L-Abu-L-Phe-L-Met-NH$_2$;
H-L-Tyr-D-Ala-L-Nva-L-Phe-L-(N-Me)Met-NH$_2$;
H-L-Tyr-D-Ala-L-Leu-L-Phe-L-(N-Me)Met-NH$_2$;
H-L-Tyr-D-Ala-L-Ile-L-Phe-L-Met-NH$_2$;
H-L-Tyr-D-Ala-L-Ile-L-Phe-L-(N-Et)Met-NH$_2$;
H-L-Tyr-D-Val-L-Ala-L-Phe-L-(N-Me)Met-NH$_2$;
H-L-Tyr-D-Leu-L-Ala-L-Phe-L-(N-Me)Met-NH$_2$;
H-L-Tyr-D-Val-L-Val-L-Phe-L-(N-Et)Met-NH$_2$;
H-L-Tyr-D-Leu-L-Leu-L-Phe-L-(N-Me)Met-NH$_2$;
H-L-Tyr-D-Ala-Gly-L-Phe-L-Nle-NH$_2$;
H-L-Tyr-D-Ala-Gly-L-Phe-L-Hse(Me)-NH$_2$;
H-L-Tyr-D-Ala-Gly-L-Phe-L-(N-Me)Nle-NH$_2$;
H-L-Tyr-D-Ala-Gly-L-Phe-L-(N-Me)Hse(Me)-NH$_2$;
H-L-Tyr-D-Ala-Gly-L-Phe-N(Me)(3-methoxypropyl);
H-L-Tyr-D-Ala-Gly-L-Phe-NH(3-methoxypropyl);
H-L-Tyr-D-Ala-Gly-L-Phe-N(Me)(3-methylthiopropyl);
H-L-Tyr-D-Ala-Gly-L-Phe-NH(3-methylthiopropyl);
H-L-Tyr-D-Ala-Gly-L-Phe-N(Me)(n-pentyl);
H-L-Tyr-D-Ala-Gly-L-Phe-NH(n-pentyl);
H-L-Tyr-D-(N-ME)Ala-Gly-L-Phe-L-Met-NH$_2$;
H-L-Tyr-D-(N-Me)Ala-Gly-L-Phe-L-(N-Me)Met-NH$_2$;
H-L-Tyr-D-(N-Me)Ala-L-Ala-L-Phe-L-Met-NH$_2$;
H-L-Tyr-D-(N-Me)Ala-L-Ala-L-Phe-L-(N-Me)Met-NH$_2$;
H-L-Tyr-D-(N-Et)Ala-Gly-L-Phe-L-(N-Me)Met-NH$_2$;
H-L-Tyr-D-(N-Me)Val-Gly-L-Phe-L-(N-Me)Met-NH$_2$;
H-L-Tyr-D-(N-Me)Leu-Gly-L-Phe-L-(N-Me)Nle-NH$_2$;
H-L-Tyr-D-(N-Me)Ile-L-Ala-L-Phe-L-(N-Me)Hse(Me)-NH$_2$;
H-L-Tyr(Ac)-D-Ala-Gly-L-Phe-L-Met-NH$_2$;
H-L-Tyr(Ac)-D-Ala-Gly-L-Phe-L-(N-Me)Met-NH$_2$;
H-L-Tyr-D-Nle-L-Nva-L-Phe-L-Met-NH$_2$;
H-L-Tyr-D-Abu-L-Abu-L-Phe-L-(N-Me)Met-NH$_2$;
(N-Me)-L-Tyr-D-Ala-Gly-L-Phe-L-Met-NH$_2$;
(N,N-Di-Me)-L-Tyr-D-Ala-L-Ala-L-Phe-L-(N-Me)-Met-NH$_2$;
(N-Allyl)-L-Tyr-D-Ala-Gly-L-Phe-L-(N-Me)Met-NH$_2$;
(N-Et)-L-Tyr-D-Abu-L-Ala-L-Phe-L-(N-Et)Nle-NH$_2$;
(N,N-di-Pr)-L-Tyr-D-Val-L-Ala-L-Phe-L-(N-Me)Hse(Me)-NH$_2$;
(N-Pr)-L-Tyr-D-Leu-Gly-L-Phe-L-(N-Me)Met-NH$_2$;
(N,N-Di-Et)-L-Tyr-D-(N-Pr)Abu-L-Ala-L-Phe-L-Met-NH$_2$;
(N-Me,N-Et)-L-Tyr(Ac)-D-(N-Pr)Nle-L-Ala-L-Phe-L-(N-Me)Met-NH$_2$;
(N,N-Di-Me)-L-Tyr(Ac)-D-(N-Et)Ile-L-Val-L-Phe-L-(N-Pr)Met-NH$_2$;
(N-Me)-L-Tyr(Ac)-D-(N-Me)Leu-Gly-L-Phe-L-(N-Et)Nle-NH$_2$;

(N-Me)-L-Tyr(Ac)-D-(N-Me)Nva-L-Nva-L-Phe-L-(N-Me)Hse(Me)-NH₂;
(N-Me)-L-Tyr-D-(N-Me)Ala-L-Nva-L-Phe-NH(3-methoxypropyl);
(N-Et)-L-Tyr(Ac)-D-(N-Me)Abu-Gly-L-Phe-NH(3-methylthiopropyl);
(N-Pr)-L-Tyr(Ac)-D-(N-Me)Val-L-Leu-L-Phe-NH(n-pentyl);
H-L-Tyr-D-Ala-Gly-L-(N-Me)Phe-L-Met-NH₂;
H-L-Tyr-D-Ala-Gly-L-(N-Me)Phe-L-(N-Me)Met-NH₂;
H-L-Tyr-D-Ala-Gly-L-(N-Et)Phe-L-(N-Me)Nle-NH₂;
H-L-Tyr-D-Ala-Gly-L-(N-Pr)Phe-L-(N-Me)Hse(Me)-NH₂;
H-L-Tyr-D-Ala-Gly-L-(N-Pr)Phe-L-(N-Me)Met-NH₂;
H-L-Tyr-D-Ala-L-Ala-L-(N-Me)Phe-L-Met-NH₂;
H-L-Tyr-D-Ala-L-Ala-L-(N-Et)Phe-L-(N-Me)Met-NH₂;
H-L-Tyr-D-Ala-L-Val-L-(N-Me)Phe-NH(n-pentyl);
H-L-Tyr-D-Ala-Gly-L-Phe-L-Met-NH(Me);
H-L-Tyr-D-Ala-Gly-L-Phe-L-(N-Me)Met-NH(Me);
H-L-Tyr-D-Ala-Gly-L-Phe-L-(N-Et)Met-NH(Me);
H-L-Tyr-D-Ala-Gly-L-Phe-L-(N-Me)Met-NH(Et);
H-L-Tyr-D-Ala-Gly-L-Phe-L-(N-Et)Met-NH(Et);
H-L-Tyr-D-Ala-Gly-L-Phe-L-(N-Me)Nle-NH(Me);
H-L-Tyr-D-Ala-Gly-L-Phe-L-(N-Et)Met-NH(Pr);
H-L-Tyr-D-Ala-Gly-L-Phe-L-(N-Pr)Met-NH(Me);
H-L-Tyr-D-Ala-Gly-L-Phe-L-Met-NH(Pr);
N,N-Di-Me)-L-Tyr-D-Ala-Gly-L-Phe-L-(N-Me)Met-NH(Et);
(N,N-Di-Me)-L-Tyr-D-(N-Me)Ala-Gly-L-(N-Me)Phe-L-(N-Me)Met-NH₂;
(N,N-Di-Et)-L-Tyr-D-(N-Me)Ala-Gly-L-(N-Et)Phe-L-(N-Et)Met-NH(Me);
(N-allyl)-L-Tyr-D-(N-Me)Ala-L-Ala-L-(N-Me)Phe-L-(N-Me)Nle-NH(Me);
(N-Me)-L-Tyr-D-Ala-L-Val-L-(N-Me)Phe-L-(N-Pr)Hse(Me)-NH(Me);
(N,N-Di-Me)-L-Tyr-D-Val-L-Ala-L-(N-Me)Phe-L-(N-Me)Met-NH(Me);
(N,N-Di-Pr)-L-Tyr-D-Ala-Gly-L-(N-Pr)Phe-L-(N-Me)Met-NH(Me);
(H-L-Tyr-D-Ala-Gly-L-(N-Me)Phe-L-Met-NH(Me);
(N-Me)-L-Tyr-D-Ala-L-Abu-L-(N-Et)Phe-N(Et)(3-methoxypropyl);
H-L-Tyr-D-Ala-Gly-L-Phe-N(Pr)(3-methylthiopropyl);
H-L-Tyr-D-Ala-Gly-L-Phe-N(Pr)(n-pentyl);
(N,N-Di-Me)-L-Tyr(Ac)-D-(N-Pr)Ala-Gly-L-(N-Et)Phe-L-(N-Me)Met-N(Di-Me);
(N,N-Di-Pr)-L-Tyr(Ac)-D-(N-Et)Val-L-Nva-L-(N-Me)Phe-L-(N-Me)Met-NH(Me);
(N-allyl)-L-Tyr(Ac)-D-(N-Pr)Ile-L-Nle-L-(N-Pr)Phe-L-(N-Pr)Nle-NH(Et);
(N-Me)-L-Tyr(Ac)-D-(N-Pr)Leu-L-Abu-L-(N-Me)-Phe-L-(N-Me)Hse(Me)-NH(Pr);
H-L-Tyr-D-Ala-Gly-L-Phe-L-Ser(Et)-NH₂;
H-L-Tyr-D-Ala-Gly-L-Phe-L-(N-Me)Leu-NH₂;
H-L-Tyr-D-Abu-Gly-L-Phe-L-Cys(p-methoxy-Bzl)-NH₂;
H-L-Tyr-D-Abu-Gly-L-Phe-L-(N-Me)Leu-NH₂;
H-L-Tyr-D-Nva-Gly-L-Phe-L-(N-Me)Leu-NH₂;
H-L-Tyr-D-Nva-Gly-L-Phe-L-Ser(p-methoxy-Bzl)-NH₂;
H-L-Tyr-D-Val-Gly-L-Phe-L-(N-Me)Leu-NH₂;
H-L-Tyr-D-Val-Gly-L-Phe-L-Ser(Me)-NH₂;
H-L-Tyr-D-Nle-Gly-L-Phe-L-Cys(Me)-NH₂;
H-L-Tyr-D-Nle-Gly-L-Phe-L-(N-Et)Leu-NH₂;
H-L-Tyr-D-Leu-Gly-L-Phe-L-Ser(Bzl)-NH₂;
H-L-Tyr-D-Leu-Gly-L-Phe-L-(N-Pr)Leu-NH₂;
H-L-Tyr-D-Ile-Gly-L-Phe-L-Cys(Bzl)-NH₂;
H-L-Tyr-D-Ile-Gly-L-Phe-L-(N-Pr)Leu-NH₂;
H-L-Tyr-D-Ala-Gly-L-Phe-L-(N-Et)Leu-NH₂;
H-L-Tyr-D-Ala-Gly-L-Phe-L-(N-Pr)Leu-NH₂;
H-L-Tyr-D-Ala-D-Ala-L-Phe-L-(N-Pr)Leu-NH₂;
H-L-Tyr-D-Ala-L-Ala-L-Phe-L-Ser(Pr)-NH₂;
H-L-Tyr-D-Ala-L-Ala-L-Phe-L-(N-Me)Leu-NH₂;
H-L-Tyr-D-Ala-L-Abu-L-Phe-L-Ser(Ip)-NH₂;
H-L-Tyr-D-Ala-L-Nva-L-Phe-L-(N-Me)Leu-NH₂;
H-L-Tyr-D-Ala-L-Leu-L-Phe-L-(N-Me)Leu-NH₂;
H-L-Tyr-D-Ala-L-Ile-L-Phe-L-Cys(i-Bu)-NH₂;
H-L-Tyr-D-Ala-L-Ile-L-Phe-L-(N-Et)Leu-NH₂;
H-L-Tyr-D-Val-L-Ala-L-Phe-L-(N-Me)Leu-NH₂;
H-L-Tyr-D-Leu-L-Ala-L-Phe-L-(N-Me)Leu-NH₂;
H-L-Tyr-D-Val-L-Val-L-Phe-L-(N-Et)Leu-NH₂;
H-L-Tyr-D-Leu-L-Leu-L-Phe-L-(N-Me)Leu-NH₂;
H-L-Tyr-D-Ala-Gly-L-Phe-L-Ser(p-methoxy-Bzl)-NH₂;
H-L-Tyr-D-Ala-Gly-L-Phe-L-Cys(Et)-NH₂;
H-L-Tyr-D-Ala-Gly-L-Phe-L-(N-Me)Ser(Et)-NH₂;
H-L-Tyr-D-Ala-Gly-L-Phe-L-(N-Me)Cys(Et)-NH₂;
H-L-Tyr-D-Ala-Gly-L-Phe-N(Me)(3-methylbutyl);
H-L-Tyr-D-Ala-Gly-L-Phe-NH(2-ethoxyethyl);
H-L-Tyr-D-Ala-Gly-L-Phe-N(Me)(3-methylbutyl);
H-L-Tyr-D-Ala-Gly-L-Phe-NH(2-ethylthioethyl);
H-L-Tyr-D-Ala-Gly-L-Phe-N(Me)[2-(p-methoxybenzyloxy)ethyl];
H-L-Tyr-D-Ala-Gly-L-Phe-NH[2-(p-methoxybenzylthio)ethyl];
H-L-Tyr-D-(N-Me)Ala-Gly-L-Phe-L-Ser(Et)-NH₂;
H-L-Tyr-D-(N-Me)Ala-Gly-L-Phe-L-(N-Me)Leu-NH₂;
H-L-Tyr-D-(N-Me)Ala-L-Ala-L-Phe-L-Cys(Et)-NH₂;
H-L-Tyr-D-(N-Me)Ala-L-Ala-L-Phe-L-(N-Me)Leu-NH₂;
H-L-Tyr-D-(N-Et)Ala-Gly-L-Phe-L-(N-Me)Leu-NH₂;
H-L-Tyr-D-(N-Me)Val-Gly-L-Phe-L-(N-Me)Leu-NH₂;
H-L-Tyr-D-(N-Me)Leu-Gly-L-Phe-L-(N-Me)Leu-NH₂;
H-L-Tyr-D-(N-Me)Ile-L-Ala-L-Phe-L-(N-Me)Ser(p-chloro-Bzl)-NH₂;
H-L-Tyr(Ac)-D-Ala-Gly-L-Phe-L-Ser(m-trifluoromethyl-Bzl)-NH₂;
H-L-Tyr(Ac)-D-Ala-Gly-L-Phe-L-(N-Me)Leu-NH₂;
H-L-Tyr-D-Nle-L-Nva-L-Phe-L-Cys(o-methyl-Bzl)-NH₂;
H-L-Tyr-D-Abu-L-Abu-L-Phe-L-(N-Me)Leu-NH₂;
(N-Me)-L-Tyr-D-Ala-Gly-L-Phe-L-Ser(p-methoxy-Bzl)-NH₂;
(N,N-Di-Me)-L-Tyr-D-Ala-L-Ala-L-Phe-L-(N-Me)-Leu-NH₂;
(N-Allyl)-L-Tyr-D-Ala-Gly-L-Phe-L-(N-Me)Leu-NH₂;
(N-Et)-L-Tyr-D-Abu-L-Ala-L-Phe-L-(N-Et)Leu-NH₂;
(N,N-di-Pr)-L-Tyr-D-Val-L-Ala-L-Phe-L-(N-Me)Leu-NH₂;
(N-Pr)-L-Tyr-D-Leu-Gly-L-Phe-L-(N-Me)Leu-NH₂;
(N,N-Di-Et)-L-Tyr-D-(N-Pr)Abu-L-Ala-L-Phe-L-Leu-NH₂;
(N-Me,N-Et)-L-Tyr(Ac)-D-(N-Pr)Nle-L-Ala-L-Phe-L-(N-Me)Leu-NH₂;
(N,N-Di-Me)-L-Tyr(Ac)-D-(N-Et)Ile-L-Val-L-Phe-L-(N-Pr)Leu-NH₂;
(N-Me)-L-Tyr(Ac)-D-(N-Me)Leu-Gly-L-Phe-L-(N-Et)Leu-NH₂;

(N-Me)-L-Tyr(Ac)-D-(N-Me)Nva-L-Nva-L-Phe-L-(N-Me)Ser(t-Bu)-NH₂;
(N-Me)-L-Tyr-D-(N-Me)Ala-L-Nva-L-Phe-NH(2-ethylthioethyl);
(N-Et)-L-Tyr(Ac)-D-(N-Me)Abu-Gly-L-Phe-NH(2-methylthioethyl);
(N-Pr)-L-Tyr(Ac)-D-(N-Me)Val-L-Leu-L-Phe-N(Me)(3-methylbutyl);
H-L-Tyr-D-Ala-Gly-L-(N-Me)Phe-L-Ser(s-Bu)-NH₂;
H-L-Tyr-D-Ala-Gly-L-(N-Me)Phe-L-(N-Me)Leu-NH₂;
H-L-Tyr-D-Ala-Gly-L-(N-Et)Phe-L-(N-Me)Cys(Et)-NH₂;
H-L-Tyr-D-Ala-Gly-L-(N-Pr)Phe-L-(N-Me)Leu-NH₂;
H-L-Tyr-D-Ala-Gly-L-(N-Pr)Phe-L-(N-Me)Cys(p-methoxy-Bzl)-NH₂;
H-L-Tyr-D-Ala-L-Ala-L-(N-Me)Phe-L-Ser(Et)-NH₂;
H-L-Tyr-D-Ala-L-Ala-L-(N-Et)Phe-L-(N-Me)Leu-NH₂;
H-L-Tyr-D-Ala-L-Val-L-(N-Me)Phe-NH(2-ethylthioethyl);
H-L-Tyr-D-Ala-Gly-L-Phe-L-Ser(Et)-NH(Me);
H-L-Tyr-D-Ala-Gly-L-Phe-L-(N-Me)Leu-NH(Me);
H-L-Tyr-D-Ala-Gly-L-Phe-L-(N-Et)Leu-NH(Me);
H-L-Tyr-D-Ala-Gly-L-Phe-L-(N-Me)Leu-NH(Et);
H-L-Tyr-D-Ala-Gly-L-Phe-L-(N-Et)Leu-NH(Et);
H-L-Tyr-D-Ala-Gly-L-Phe-L-(N-Me)Leu-NH(Me);
H-L-Tyr-D-Ala-Gly-L-Phe-L-(N-Et)Cys(p-bromo-Bzl)-NH(Pr);
H-L-Tyr-D-Ala-Gly-L-Phe-L-(N-Pr)Leu-NH(Me);
H-L-Tyr-D-Ala-Gly-L-Phe-L-Cys(Ip)-NH(Pr);
(N,N-Di-Me)-L-Tyr-D-Ala-Gly-L-Phe-L-(N-Me)Leu-NH(Et);
(N,N-Di-Me)-L-Tyr-D-(N-Me)Ala-Gly-L-(N-Me)Phe-L-(N-Me)Leu-NH₂;
(N,N-Di-Et)-L-Tyr-D-(N-Me)Ala-Gly-L-(N-Et)Phe-L-(N-Et)Leu-NH(Me);
(N-allyl)-L-Tyr-D-(N-Me)Ala-L-Ala-L-(N-Me)Phe-L-(N-Me)Leu-NH(Me);
(N-Me)-L-Tyr-D-Ala-L-Val-L-(N-Me)Phe-L-(N-Pr)Ser(Bzl)-NH(Me);
(N,N-Di-Me)-L-Tyr-D-Val-L-Ala-L-(N-Me)Phe-L-(N-Me)Leu-NH(Me);
(N,N-Di-Pr)-L-Tyr-D-Ala-Gly-L-(N-Pr)Phe-L-(N-Me)Leu-NH(Me);
H-L-Tyr-D-Ala-Gly-L-(N-Me)Phe-L-Ser(Pr)-NH(Me);
(N-Me)-L-Tyr-D-Ala-L-Abu-L-(N-Et)Phe-N(Et)(3-methylbutyl);
H-L-Tyr-D-Ala-Gly-L-Phe-N(Pr)(3-methylbutyl);
H-L-Tyr-D-Ala-Gly-L-Phe-N(Pr)(2-ethoxyethyl);
(N,N-Di-Me)-L-Tyr-(Ac)-D-(N-Pr)Ala-Gly-L-(N-Et)Phe-L-(N-Me)Leu-N(Di-Me);
(N,N-Di-Pr)-L-Tyr(Ac)-D-(N-Et)Val-L-Nva-L-(N-Me)Phe-L-(N-Me)Leu-NH(Me);
(N-allyl)-L-Tyr(Ac)-D-(N-Pr)Ile-L-Nle-L-(N-Pr)Phe-L-(N-Pr)Leu-NH(Et);
(N-Me)-L-Tyr(Ac)-D-(N-Pr)Leu-L-Abu-L-(N-Me)-Phe-L-(N-Me)Leu-NH(Pr);
and the like.

The compounds of this invention are prepared by routine methods for peptide synthesis. It is possible, during the synthesis of certain of the compounds of this invention, that partial racemization can occur. However, the extent of racemization, should such occur, is not sufficient to seriously alter the analgesic activity of the compounds of this invention.

The methods for preparing the compounds of this invention involve the coupling of amino acids or peptide fragments by reaction of the carboxyl function of one with the amino function of another to produce an amide linkage. In order to effectively achieve coupling, it is desirable, first, that all reactive functionalities not participating directly in the reaction be inactivated by the use of appropriate blocking groups, and, secondly, that the carboxyl function which is to be coupled be appropriately activated to permit coupling to proceed. All of this involves a careful selection of both reaction sequence and reaction conditions as well as utilization of specific blocking groups so that the desired peptide product will be realized. Each of the amino acids which is employed to produce the compounds of this invention and which has the particularly selected protecting groups and/or activating functionalities is prepared by employing techniques well recognized in the peptide art.

Selected combinations of blocking groups are employed at each point of the total synthesis of the compounds of this invention. These particular combinations have been found to function most smoothly. Other combinations indeed would operate satisfactorily in the synthesis of the compounds of this invention, although, perhaps, with a lesser degree of success. Thus, for example, benzyloxycarbonyl (CBz), t-butyloxycarbonyl (BOC), t-amyloxycarbonyl (AOC), p-methoxybenzyloxycarbonyl (MBOC), adamantyloxycarbonyl (AdOC), and isobornyloxycarbonyl can be variously employed as amino blocking groups in the synthesis of the compounds of this invention. Furthermore, benzyl (Bzl) generally is employed as the hydroxy-protecting group for the tyrosyl residue even though others, such as p-nitrobenzyl (PNB), p-methoxybenzyl (PMB), and the like, could well be employed.

The carboxyl blocking groups used in preparing the compounds of this invention can be any of the typical ester-forming groups, including, for example, methyl, ethyl, benzyl, p-nitrobenzyl, p-methoxybenzyl, 2,2,2-trichloroethyl, and the like.

Coupling of the suitably protected N-blocked amino acid or peptide fragment with a suitably protected carboxy-blocked amino acid or peptide fragment in preparation of the compounds of this invention consists of rendering the free carboxyl function of the amino acid or peptide fragment active to the coupling reaction. This can be accomplished using any of several well recognized techniques. One such activation technique involves conversion of the carboxyl function to a mixed anhydride. The free carboxyl function is activated by reaction with another acid, typically a derivative of carbonic acid, such as an acid chloride thereof. Examples of acid chlorides used to form mixed anhydrides are ethyl chloroformate, phenyl chloroformate, sec-butyl chloroformate, isobutyl chloroformate, pivaloyl chloride, and the like. Preferably, isobutyl chloroformate is employed.

Another method of activating the carboxyl function for the purpose of carrying out the coupling reaction is by conversion to its active ester derivative. Such active esters include, for example, a 2,4,5-trichlorophenyl ester, a pentachlorophenyl ester, a p-nitrophenyl ester, and the like. Another coupling method available for use is the well-recognized azide coupling method.

The preferred coupling method in preparation of the compounds of this invention involves the use of N,N'-dicyclohexylcarbodiimide (DCC) to activate the free carboxyl function thereby permitting coupling to proceed. This activation and coupling technique is carried out employing an equimolar quantity of DCC relative to the amino acid or peptide fragment and is carried out in the presence of an equimolar quantity of 1-hydroxybenzotriazole (HBT). The presence of HBT suppresses undesirable side reactions including the possibility of racemization.

Cleavage of selected blocking groups is necessary at particular points in the synthetic sequence employed in preparation of the compounds of this invention. A chemist of ordinary skill in the art of peptide synthesis can readily select from representative protecting groups those groups which are compatible in the sense that selective cleavage of the product can be accomplished permitting removal of one or more but less than all of the protecting groups present on the amino acid or peptide fragment. These techniques are well recognized in the peptide art. A fuller discussion of the techniques which are available for selective cleavage is provided in the literature in Schröder and Lübke, *The Peptides,* Volume I, Academic Press, New York, (1965), and especially in the Table provided at pages 72–75 thereof.

Cleavage of carboxyl protecting groups can be accomplished by alkaline saponification. Relatively strong alkaline conditions, typically using an alkali metal hydroxide, such as sodium hydroxide, potassium hydroxide, lithium hydroxide, and the like, are generally employed to deesterify the protected carboxyl. The reaction conditions under which saponification is accomplished are well recognized in the art. The carboxyl blocking groups also can be removed by catalytic hydrogenolysis including, for example, hydrogenolysis in the presence of a catalyst such as palladium on carbon. Furthermore, in those instances in which the carboxyl blocking group is p-nitrobenzyl or 2,2,2-trichloroethyl, deblocking can be accomplished by reduction in the presence of zinc and hydrochloric acid.

The amino blocking groups are cleaved by treating the protected amino acid or peptide with an acid such as formic acid, trifluoroacetic acid (TFA), p-toluenesulfonic acid (TSA), benzenesulfonic acid (BSA), naphthalenesulfonic acid, and the like, to form the respective acid addition salt product. Cleavage of the amino blocking group also can be accomplished by treating the blocked amino acid or peptide with a mixture of HBr or HCl and acetic acid to produce the corresponding hydrobromide or hydrochloride acid addition salt. The particular method or reagent which is employed will depend upon the chemical or physical characteristics of the materials involved in the specific deblocking reaction. It has been discovered, in those instances in which the group $R_7$ is other than hydrogen and a peptide containing at least three amino acid residues is to be deblocked, that it is highly preferred that the peptide be deblocked with trifluoroacetic acid or formic acid to produce the corresponding acid addition salt. The salt can be converted to a more pharmaceutically acceptable form by treatment with a suitable ion exchange resin, such as DEAE Sephadex A25, Amberlyst A27, and the like.

The hydroxy-protecting group present on the tyrosyl residue can be retained on the peptide throughout the sequence of its preparation, being removed during the final synthetic step in conjunction with cleavage of the amino blocking group. However, depending upon the conditions employed for removal of the carboxyl blocking group, it may be removed earlier in the preparative sequence. When the carboxyl group is cleaved by alkaline saponification, the hydroxy-protecting group is retained; however, when catalytic hydrogenolysis is employed for removal of the carboxyl protecting group, the hydroxy protecting group also is cleaved. The latter situation does not represent a serious problem since preparation of the compounds of this invention can be accomplished in the presence of a tyrosyl residue having a free hydroxyl group.

A preferred specific method for preparing the compounds of this invention involves coupling a separately prepared N-terminal tripeptide with a separately prepared C-terminal dipeptide amide or a C-terminal amino acid amide (in those instances in which Z is hydrogen) followed by appropriate deblocking of any remaining blocked moieties. This general sequence, illustrating preparation of a pentapeptide of this invention, can be depicted as follows. In the sequence, the symbol AA represents the amino acid residue, and the appended number represents the position of the amino acid in the ultimate peptide product sequence.

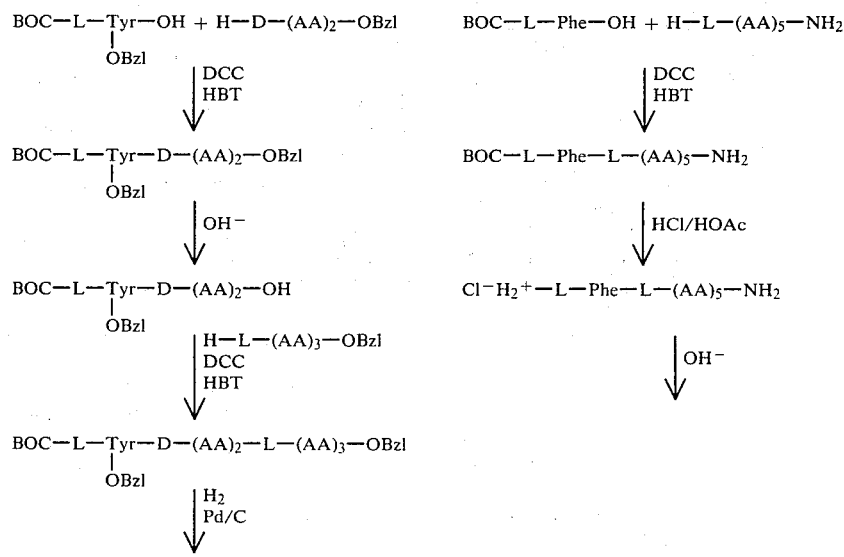

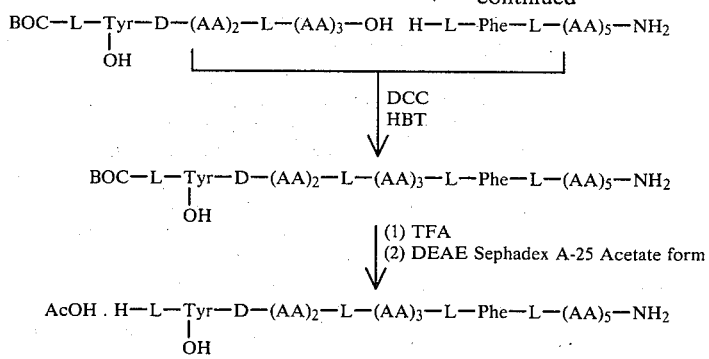

The above represents only one sequence for preparing compounds of this invention. Other sequences are available. Another method which can be employed involves the step-wise, sequential addition of single amino acids in construction of the peptide chain beginning with the carboxamide terminal amino acid. Reaction techniques such as those described above would be employed in this as well as any other contemplated preparative sequence.

In certain of the compounds of this invention, one or more of the groups $R_1$, $R_2$, $R_3$, $R_6$ and $R_7$ are $C_1$–$C_3$ primary alkyl. In addition, when $R_2$ is hydrogen, $R_1$ can be allyl. In those instances, the appropriate N-substituted amino acid is employed in the preparative sequence. Any of the N-monosubstituted amino acids can be prepared by the same sequence which is depicted as follows using an N-protected amino acid as starting material:

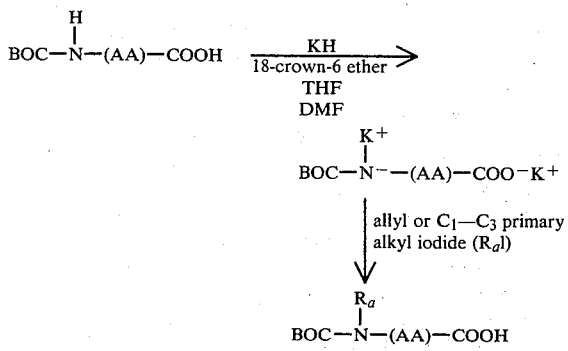

As the above sequence indicates, the amino acid first is treated with potassium hydride in the presence of a suitable crown ether to generate the dianion. The intermediate then is treated with the appropriate alkyl or allyl iodide to obtain the desired N-substituted amino acid.

It will be apparent to those of ordinary skill in the art of peptide synthesis that racemization at the α-carbon can occur under strongly alkaline conditions such as those employed in the above alkylation procedure. The degree of racemization may vary depending upon the particular amino acid which is involved. Racemization can be minimized by using excess alkylating agent and by keeping the reaction time as short as possible. Nevertheless, even in the event that excessive racemization does occur, the product can be purified by recrystallization as the salt of a suitable chiral amine, for example, as the salt of d(+) α-phenylethylamine.

In the instances in which both $R_1$ and $R_2$ are the same $C_1$–$C_3$ primary alkyl, the desired N,N-disubstituted tyrosine can be prepared by the following sequence:

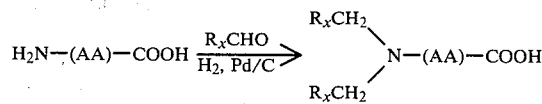

In the foregoing, $R_xCHO$ represents formaldehyde, acetaldehyde, or propionaldehyde.

In those instances in which $R_1$ and $R_2$ are different $C_1$–$C_3$ primary alkyl groups, the N,N-disubstituted tyrosine is available by treating the appropriate N-monosubstituted tyrosine, prepared in accordance with the foregoing sequence, with formaldehyde or acetaldehyde as described hereinabove.

The C-terminal portion of the peptides of this invention is derivatized to its amide. In the pentapeptides of this invention, the amide is unsubstituted or N-monosubstituted. In the tetrapeptides of this invention, the amide is N-monosubstituted or N,N-disubstituted. Derivatization to the amide is accomplished by activation of the carboxyl group of the amino acid with N,N'-dicyclohexylcarbodiimide (DCC) in the presence of 1-hydroxybenzotriazole (HBT) to give the HBT ester. In producing the pentapeptides of this invention, the ester then is reacted with anhydrous ammonia or the appropriate primary amine to give the unsubstituted or N-monosubstituted amide. Suitable primary amines for preparation of the pentapeptides of this invention include methylamine, ethylamine, and n-propylamine. When the compounds of this invention are the tetrapeptides, the ester is reacted with an appropriate primary or secondary amine. Suitable such amines include 3-(methylthio)propylamine, 3-(methoxy)propylamine, n-pentylamine,
N-[3-(methylthio)propyl]-N-methylamine,
N-[3-(methylthio)propyl]-N-ethylamine,
N-[3-(methylthio)propyl]-N-propylamine,
N-[3-(methoxy)propyl]-N-methylamine,
N-[3-(methoxy)propyl]-N-ethylamine,
N-[3-(methoxy)propyl]-N-propylamine,
N-n-pentyl-N-propylamine,
N-n-pentyl-N-ethylamine,
N-n-pentyl-N-methylamine,
N-(3-methylbutyl)-N-methylamine,
N-(3-methylbutyl)-N-ethylamine,
N-(3-methylbutyl)-N-propylamine,
2-ethoxyethylamine,
2-methoxyethylamine,
2-propoxyethylamine, 2-butoxyethylamine,
2-benzyloxyethylamine,
2-(p-methoxy)benzyloxyethylamine,
2-methylthioethylamine,
2-ethylthioethylamine,
2-propylthioethylamine,
2-benzylthioethylamine,
2-(p-methoxy)benzylthioethylamine,
N-methyl-N-(2-ethoxyethyl)amine,
N-methyl-N-(2-ethylthio)ethylamine,
N-methyl-N-(2-benzyloxy)ethylamine,
N-methyl-N-(2-p-methoxybenzyloxy)ethylamine,
N-methyl-N-(2-p-methoxybenzylthio)ethyl,
and the like.

Those compounds of this invention in which Y is acetyl are prepared from the corresponding peptide in which Y is hydrogen and the terminal amino group is suitably blocked. This latter compound is treated with acetic anhydride in the presence of pyridine to produce the corresponding N-blocked, O-acetyl peptide. Upon deblocking with a mixture of hydrochloric acid and acetic acid, the desired compound is obtained.

The compounds of this invention are valuable pharmaceutical agents. They exhibit analgesic activity, and they especially are useful upon parenteral administration to mammals, including humans.

The compounds of this invention can be administered as such, or they can be compounded and formulated into pharmaceutical preparations in unit dosage form for parenteral administration. In the compounding or formulation, organic or inorganic solids and/or liquids which are pharmaceutically acceptable carriers can be employed. Suitable such carriers will be well recognized by those of ordinary skill in the art. The compositions may take the form of tablets, powder granules, capsules, suspensions, solutions, and the like.

The compounds of this invention, when administered in an effective amount, will produce an analgesic effect. Dose levels may range generally from about 0.1 milligram to about 100 milligrams per kilogram body weight of the recipient. The preferred dose range generally is from about 1.0 milligram to about 20 milligrams per kilogram body weight of the recipient.

The following examples are provided to illustrate the preparation and activity of the compounds of this invention. They are not intended to be limiting upon the scope thereof.

EXAMPLE 1

Preparation of
L-Tyrosyl-D-alanyl-glycyl-L-phenylalanyl-$N^\alpha$-methyl-L-methionylamide Hydrochloride A. Benzyl D-Alinate p-Toluenesulfonate.

To a mixture of 100 ml. of benzyl alcohol and 200 ml. of benzene containing 55.1 g (0.29 mole) of p-toluenesulfonic acid monohydrate was added 25 g. (0.281 mole) of D-alanine. The mixture was brought to reflux, and water was removed azeotropically in a Dean-Stark apparatus. The mixture was heated for fifteen hours and then was cooled to room temperature and diluted with ether. The resulting precipitate was collected and recrystallized from methanol-ether to afford 55.3 g. (56%) of the title compound, m.p. 112°–115° C.

Analysis, calculated for $C_{17}H_{21}NO_5S$ (351.42): C, 58.10; H, 6.02; N, 3.99. Found: C, 58.19; H, 6.06; N, 3.82.

B. Benzyl $N^\alpha$-t-Butyloxycarbonyl-O-benzyl-L-tyrosyl-D-alinate.

To 200 ml. of dry N,N-dimethylformamide (DMF) was added 35.1 g. (0.1 mole) of the product from Part A. The resulting mixture was stirred and cooled to 0° C., and 11.2 g. (0.1 mole) of diazabicyclooctane (DABCO) was added. The mixture was stirred for ten minutes at 0° C., and 37.1 g. (0.1 mole) of $N^\alpha$-t-butyloxycarbonyl-O-benzyl-L-tyrosine was added followed by 13.5 g. (0.1 mole) of 1-hydroxybenzotriazole (HBT) and 20.6 g. (0.1 mole) of N,N'-dicyclohexylcarbodiimide (DCC). The resulting mixture was stirred at 0° C. for three hours and then at room temperature for twenty-four hours. The mixture then was cooled to 0° C., the resulting suspension was filtered, and the filtrate was concentrated in vacuo. The resulting residue then was redissolved in ethyl acetate and was washed successively with 1 N $NaHCO_3$, water, 0.75 N cold citric acid, and water. The organic layer then was dried over magnesium sulfate, filtered, and concentrated in vacuo. The resulting residue then was dissolved in hot ethanol. Crystallization ensued upon cooling. After one recrystallization from ethanol, 41.5 g. (80%) of pure title compound was obtained, m.p. 121°–123° C.

Analysis, calculated for $C_{30}H_{36}N_2O_6$ (520.63): C, 69.21; H, 6.97; N, 5.38. Found: C, 68.99; H, 6.75; N, 5.17.

C. $N^\alpha$-t-Butyloxycarbonyl-O-benzyl-L-tyrosyl-D-alanine.

To a mixture of 200 ml. of tetrahydrofuran (THF) and 20 ml. of water was added 31.2 g. (0.06 mole) of the product from Part B. The resulting solution was cooled to 0° C., and 13.2 ml. (1.1 equiv.) of 5 N sodium hydroxide was added slowly. The resulting mixture was stirred and allowed slowly to warm to room temperature. After five hours, the mixture was partitioned between water and ether. The aqueous layer was separated and cooled, the pH was adjusted to 2 by addition of citric acid, and the mixture was extracted with ethyl acetate. The ethyl acetate extract was washed with water, dried over magnesium sulfate, filtered, and diluted with ether. The resulting precipitate was collected to afford 17.7 g (67%) of the title compound, m.p. 160°–162° C.

Analysis, calculated for $C_{24}H_{30}N_2O_6$ (442.51): C, 65.14; H, 6.83; N, 6.63. Found: C, 64.73; H, 6.70; N, 6.20.

D. Benzyl $N^\alpha$-t-Butyloxycarbonyl-O-benzyl-L-tyrosyl-D-alanyl-glycinate.

To 70 ml. of dry DMF was added 6.74 g. (0.02 mole) of the p-toluenesulfonic acid salt of benzyl glycinate. The resulting mixture was cooled to 0° C., and 2.24 g. (0.020 mole) of DABCO was added. The mixture was stirred for a few minutes, and 8.84 g. (0.020 mole) of the product of Part C was added followed by 2.7 g. (0.020 mole) of the HBT and 4.12 g. (0.020 mole) of DCC. The reaction mixture was stirred for two hours at 0° C. and then for twenty-four hours at room temperature. The resulting suspension was cooled to 0° C., filtered, and the filtrate was concentrated in vacuo. The resulting residue was dissolved in ethyl acetate and was washed successively with 1 N sodium bicarbonate, water, cold 0.75 N citric acid, and water. The organic phase was dried over magnesium sulfate, filtered, and concentrated in vacuo. The resulting residue was crystallized from ethanol to give 10.8 g. (92%) of pure title compound, m.p. 145°–147° C.

Analysis, calculated for $C_{33}H_{39}N_3O_7$ (589.69): C, 67.22; H, 6.67; N, 7.13. Found: C, 67.32; H, 6.83; N, 6.91.

E. $N^\alpha$-t-Butyloxycarbonyl-L-tyrosyl-D-alanyl-glycine.

To 60 ml. of DMF was added 10.5 g. (0.018 mole) of the product from Part D followed by 2.5 g. of 5% Pd/C added as a DMF slurry. The resulting mixture was flushed with nitrogen, and hydrogen was introduced via a gas dispersion tube at atmospheric pressure and room temperature. After 3.5 hours, the hydrogen flow was terminated, and the catalyst was removed by filtration. The filtrate was concentrated in vacuo. Trituration of the residue with ether gave 5.4 g. (75%) of the title compound as amorphous solid.

Analysis, calculated for $C_{26}H_{26}N_2O_5$ (446.65): C, 69.94; H, 5.87; N, 6.27. Found: C, 70.08; H, 5.82; N, 6.16.

F. $N^\alpha$-t-Butyloxycarbonyl-$N^\alpha$-methyl-L-methionylamide.

The dicyclohexylamine salt of $N^\alpha$-t-butyloxycarbonyl-L-methionine (17.2 g.; 0.04 mole) was partitioned between ethyl acetate and cold 0.75 N citric acid. The resulting organic phase was separated, washed with water, dried over magnesium sulfate, filtered, and concentrated in vacuo to an oily residue. The residue was dissolved in a mixture of 80 ml. of dry THF and 10 ml. of DMF, and 0.5 g. of 18-crown-6 ether was added. A potassium hydride suspension (equivalent 0.12 mole) was stirred and added dropwise to the resulting cooled mixture over thirty minutes. Methyl iodide (2.49 ml.; 0.04 mole) was added, and the mixture was stirred for twenty-four hours at room temperature. The reaction mixture then was cooled and acidified to pH 3 with 0.75 N citric acid and then was partitioned between water and ether. The ether layer was washed with water several times and then was extracted with 1 N sodium bicarbonate. The aqueous extracts were combined, acidified to pH 2, and extracted with ethyl acetate. The ethyl acetate extract was dried over magnesium sulfate, filtered, and evaporated in vacuo to give 8.4 g. of product having an nmr spectrum consistent with the desired N-methylated product. [$\delta$2.92, N—CH$_3$; $\delta$2.11, S—CH$_3$; $\delta$1.6, C(CH$_3$)$_3$].

The oil (8.4 g.; approximately 0.034 mole) then was dissolved in 60 ml. of DMF. The solution was cooled to 0° C., and 4.69 g. (0.035 mole) of HBT and 7.0 g. (0.034 mole) of DCC were added. The mixture was stirred for two hours at 0° C., and anhydrous ammonia was bubbled into the mixture via a gas dispersion tube for 45 minutes. The reaction mixture then was filtered, and the filtrate was concentrated in vacuo. The resulting residue was applied to a 3×50 cm. silica gel (60-200 mesh) column and was eluted with chloroform followed by a 9.75:0.25 mixture of chloroform and methanol. Thin-layer chromatography (TLC) analysis of the fractions from the column and subsequent combination on the basis of the TLC profile gave, after concentration in vacuo, product which was twice recrystallized from a mixture of ether and petroleum ether to afford 4.1 g. (39%) of the title compound, m.p. 75°–78° C.

nmr: $\delta$2.80, N—CH$_3$; $\delta$2.10, S—CH$_3$; $\delta$1.48, C(CH$_3$)$_3$. $[\alpha]_D^{25}$ −29.5 (C=0.5, CHCl$_3$).

Analysis, calculated for $C_{11}H_{22}N_2O_3S$ (262.37): C, 50.36; H, 8.45; N, 10.68. Found: C, 50.59; H, 8.24; N, 10.87.

G. $N^\alpha$-t-Butyloxycarbonyl-L-phenylalanyl-$N^\alpha$-methyl-L-methionylamide.

A mixture of 20 ml. of glacial acetic acid, 2 ml. of anisole, 2 ml. of triethylsilane, and 3.8 g. (0.0144 mole) of the product from Part F was prepared. Anhydrous hydrogen chloride was bubbled into the resulting mixture for thirty minutes. The mixture then was diluted with ether. The precipitate which resulted was filtered, dried (2.9 g.), and then was redissolved in 40 ml. of DMF. The mixture was cooled to 0° C., and 2.9 ml. (0.0146 mole) of dicyclohexylamine was added followed by 1.97 g. (0.0146 mole) of HBT, 3.87 g. (0.0146 mole) of $N^\alpha$-t-butyloxycarbonyl-L-phenyl-alanine, and 3.0 g. (0.0146 mole) of DCC. The resulting mixture was stirred for two hours at 0° C., and then for twenty-four hours at room temperature. The mixture was cooled to 0° C. and filtered. The resulting filtrate then was concentrated in vacuo. The residue was redissolved in ethyl acetate, and the solution was washed successively with 1 N sodium bicarbonate, water, 0.75 N citric acid, and water. The ethyl acetate solution then was dried over magnesium sulfate and evaporated in vacuo to provide an oil which would not crystallize from petroleum ether. The residue then was applied to a 3×50 cm. silica gel (60-200 mesh) column and was eluted with chloroform followed by chloroform-methanol (9.8:0.2). TLC analysis of the fractions from the column and subsequent combination on the basis of the TLC profile gave, upon evaporation of the chromatography solvent, a residue which was crystallized from ether-petroleum ether to afford 3.1 g. (52.5%) of the title compound, m.p. 99°–103° C.

Analysis, calculated for $C_{20}H_{31}N_3O_4S$ (409.55): C, 58.65; H, 7.63; N, 10.26. Found: C, 58.74; H, 7.47; N, 10.45.

H. $N^\alpha$-t-Butyloxycarbonyl-L-tyrosyl-D-alanyl-glycyl-L-phenylalanyl-$N^\alpha$-methyl-L-methionylamide.

To a mixture of 20 ml. of glacial acetic acid, 3 ml. of anisole, and 3 ml. of triethylsilane were added 2.2 g. (5.37 mmoles) of the product from Part G. Dry hydrogen chloride was bubbled into the mixture for thirty minutes. Ether was added to the mixture, and a solid precipitated and was filtered and dried in vacuo. The solid (1.75 g.; 5 mmoles) was dissolved in 30 ml. of dry DMF, and the mixture was cooled to 0° C. The hydrochloride salt then was neutralized by addition of 0.99 ml. (5 mmoles) of dicyclohexylamine. After five minutes, 2.05 g. (5 mmoles) of the product from Part E were added followed by 0.68 g. (5 mmoles) of HBT and 1.03 g. (5 mmoles) of DCC. The mixture then was stirred for twenty-four hours at 4° C. The resulting insoluble material was removed by filtration, and the filtrate was evaporated in vacuo. The resulting residue was re-dissolved in ethyl acetate, and the ethyl acetate was washed successively with 1 N aqueous sodium bicarbonate, cold 0.75 N citric acid, and water. The solution then was dried over magnesium sulfate and was applied to a 3×50 cm. column of silica gel (60-200 mesh) and was eluted with chloroform followed by chloroform-methanol (9:1). TLC analysis of the fractions from the column and the subsequent combination on the basis of the TLC profile gave two batches of crude product weighing 0.80 g. and 1.2 g., respectively. The first batch was further purified by preparative thick layer chromatography on silica gel (chloroform:methanol; 9:1) to give 0.62 g. of the title compound as an amorphous solid.

Analysis, calculated for $C_{34}H_{48}N_6O_8S$ (700.86): C, 58.27; H, 6.90; N, 11.99. Found: C, 58.48; H, 6.64; N, 11.97.

Amino acid analysis, Found: Tyr, 0.99; Ala, 1.00; Gly, 1.00; Phe, 1.00.

The second batch of material was twice chromatographed in the same manner as described above to afford 0.74 g. of the desired product having correct elemental and amino acid analyses.

I. L-Tyrosyl-D-alanyl-glycyl-L-phenylalanyl-$N^\alpha$-methyl-L-methionylamide hydrochloride.

To 5 ml. of glacial acetic acid containing 0.2 ml. of anisole was added 0.72 g. (1.03 mmoles) of the title compound from Part H. Anhydrous hydrogen chloride then was bubbled into the mixture for twenty minutes. The mixture was lyophilized to afford 0.74 g. of the title compound. $R_f^A$, 0.3.

An analytical sample of the product was dried in vacuo at 100° C.

Analysis, calculated for $C_{29}H_{41}N_6O_6SCl$ (637.20): C, 54.66; H, 6.49; N, 13.19. Found: C, 54.36; H, 6.19; N, 13.00.

Amino acid analysis, Found: Tyr, 1.01; Ala, 0.99; Gly, 1.00; Phe, 1.00.

EXAMPLE 2

Preparation of L-Tyrosyl-D-leucyl-glycyl-L-phenylalanyl-$N^\alpha$-methyl-L-methionylamide Sesquihydrochloride Monoacetate A. Benzyl D-Leucinate p-Toluenesulfonate.

This compound was prepared in a manner corresponding precisely to that described in Part A of Example 1 for preparation of the D-alinate compound. Yield, 73%, m.p. 155°–156° C.

Analysis, calculated for $C_{20}H_{27}NO_5S$ (393.50): C, 61.05; H, 6.92; N, 3.56. Found: C, 61.17; H, 6.68; N, 3.81.

B. Benzyl $N^\alpha$-t-Butyloxycarbonyl-O-benzyl-L-tyrosyl-D-leucinate.

To 50 ml. of DMF were added 7.86 g. (0.020 mole) of the product from Part A. The mixture was cooled to 0° C., and 2.24 g. (0.020 mole) of DABCO were added. The mixture was stirred for five minutes, and 7.42 g. (0.020 mole) of $N^\alpha$-t-butyloxycarbonyl-O-benzyl-L-tyrosine was added, followed by 2.7 g. (0.020 mole) of HBT and 4.12 g. (0.02 mole) of DCC. The resulting mixture was stirred for two hours at 0° C., and then four twenty-four hours at room temperature. The mixture then was cooled to 0° C., and the resulting suspension was filtered. The filtrate was concentrated in vacuo. The resulting residue then was dissolved in ethyl acetate, and the ethyl acetate solution was washed successively with 1 N sodium bicarbonate, water, cold 0.75 N citric acid, and water. The organic phase was dried over magnesium sulfate, filtered, and the filtrate was concentrated in vacuo. The resulting residue was crystallized from hot ethanol to afford 9.0 g. (78%) of the title compound, m.p. 100°–103° C.

Analysis, calculated for $C_{34}H_{42}N_2O_6$ (574.72): C, 71.06; H, 7.37; N, 4.87. Found: C, 71.30; H, 7.15; N, 4.79.

C. $N^\alpha$-t-Butyloxycarbonyl-O-benzyl-L-tyrosyl-D-leucine.

To 80 ml. of THF was added 8.0 g. (0.0139 mole) of the product from Part B. After the addition of 20 ml. of water, the resulting mixture was cooled to 0° C., and 7.25 ml. (0.0145 mole) of 2 N sodium hydroxide was added slowly. Upon completion of the addition, the mixture was stirred at 0° C. for thirty minutes and then at room temperature for four hours. The reaction mixture then was partitioned between water and ether. The aqueous phase was separated, cooled to 0° C., acidified to pH 2 with cold 1 N HCl, and extracted with ethyl acetate. The ethyl acetate extract then was washed with water, dried over magnesium sulfate, filtered, and concentrated in vacuo to provide a syrupy residue. The residue was crystallized from ether-petroleum ether to provide 6.4 g. (95%) of the title compound, m.p. 90°–94° C.

Analysis, calculated for $C_{27}H_{36}N_2O_6$ (484.59): C, 66.92; H, 7.49; N, 5.78. Found: C, 67.14; H, 7.38; N, 5.76.

D. Benzyl $N^\alpha$-t-Butyloxycarbonyl-O-benzyl-L-tyrosyl-D-leucyl-glycinate.

A mixture of 3.37 g. (0.010 mole) of the p-toluenesulfonate salt of benzyl glycinate and 1.12 g. (0.010 mole) of DABCO in 25 ml. of dry DMF was prepared. To the mixture was added 4.84 g. (0.010 mole) of the compound from Part C. The mixture then was cooled to 0° C., and 1.35 g. (0.010 mole) of HBT and 2.06 g. (0.010 mole) of DCC were added. The resulting mixture was stirred for two hours at 0° C. and then for twenty-four hours at room temperature. The mixture was cooled to 0° C., filtered, and the filtrate was concentrated in vacuo. The resulting residue was dissolved in ethyl acetate, and the ethyl acetate solution was washed successively with 1 N sodium bicarbonate, water, cold 0.75 N citric acid, and water. The solution then was dried over magnesium sulfate, filtered, and concentrated in vacuo. The resulting residue was crystallized from ethanol-water to provide 4.0 g. (63%) of the title compound, m.p. 114°–116° C.

Analysis, calculated for $C_{36}H_{45}N_3O_7$ (631.77): C, 68.44; H, 7.18; N, 6.65. Found: C, 68.17; H, 7.12; N, 6.40.

E. $N^\alpha$-t-Butyloxycarbonyl-L-tyrosyl-D-leucyl-glycine.

To 5 ml. of anhydrous DMF was added 3.9 g. (0.006 mole) of the compound from Part D followed by 1.5 g. of 5% Pd/C. To the mixture then was added 40 ml. of ethanol, the mixture was flushed with nitrogen, and hydrogen was introduced for five hours, the mixture being maintained at atmospheric pressure and at room temperature. The catalyst then was filtered from the mixture, and the filtrate was evaporated in vacuo. The resulting residue was crystallized from ether-ethyl acetate to provide 2.3 g. (85%) of the title compound, m.p. 189°–190° C.

Analysis, calculated for $C_{22}H_{33}N_3O_7$ (451.52): C, 58.52; H, 7.37; N, 9.31. Found: C, 58.79; H, 7.48; N, 9.39.

F. $N^\alpha$-t-Butyloxycarbonyl-L-tyrosyl-D-leucyl-glycyl-L-phenylalanyl-$N^\alpha$-methyl-L-methionylamide.

To 10 ml. of anhydrous DMF were added 0.692 g. (0.002 mole) of the hydrochloride salt of L-phenylalanyl-$N^\alpha$-methyl-L-methionylamide (prepared as in Part H of Example 1) and 0.903 g. (0.002 mole) of the product from Part E. The resulting mixture was cooled to 0° C., and 0.28 ml. (0.002 mole) of triethylamine was added followed, after ten minutes, by 0.27 g. (0.002 mole) of HBT and 0.412 g. (0.002 mole) of DCC. The mixture then was stirred at 0° C. for two hours and then at 4° C. for twenty-four hours. The resulting precipitate was removed by filtration, and the filtrate was concentrated in vacuo to a residue which then was dissolved in ethyl acetate. The ethyl acetate solution was washed successively with 1 N sodium bicarbonate, water, cold 0.75 N citric acid, and water. The organic phase then was dried over magnesium sulfate, filtered, and the filtrate was concentrated in vacuo. The residue was applied to two preparative thick layer chromatography plates, and the plates were eluted with chloroform-methanol (9.25:0.75). The major UV positive band was cut from each plate, and the product was eluted from the silica gel with chloroform-methanol. The solvent was removed in vacuo to give 1.2 g. (81%) of the title compound as in amorphous solid. $[\alpha]_D^{25}$ −31.5 (C=0.5, MeOH)

Analysis, calculated for $C_{37}H_{54}N_6O_8S$ (742.93): C, 59.82; H, 7.33; N, 11.31. Found: C, 59.88; H, 7.06; N, 11.15.

Amino acid analysis, Found: Tyr, 1.01; Leu, 1.00; Gly, 1.00; Phe, 0.99.

G. L-Tyrosyl-D-leucyl-glycyl-L-phenylalanyl-$N^\alpha$-methyl-L-methionylamide Sesquihydrochloride Monoacetate.

To 5 ml. of glacial acetic acid containing 0.3 ml. of anisole was added 0.900 g. (0.0012 mole) of the compound of Part F. Dry hydrogen chloride was bubbled into the mixture for twenty minutes. The solvent then was removed by lyophilization from aqueous acetic acid to give the title compound as an amorphous solid. $[\alpha]_D^{25} -2.1$ [C=0.3, MeOH]

Analysis, calculated for $C_{32}H_{47}N_6O_6S \cdot 1.5HCl \cdot C_2H_4O_2$ (757.04): C, 53.93; H, 6.79; N, 11.10; Cl, 7.02. Found: C, 54.30; H, 6.64; N, 11.32; Cl, 6.96.

Amino acid analysis, Found: Tyr, 0.99; Leu, 1.03; Gly, 0.99; Phe, 0.99.

EXAMPLE 3

Preparation of L-Tyrosyl-D-alanyl-glycyl-L-phenylalanyl-L-methionylamide Hydrochloride A. Methyl $N^\alpha$-t-Butyloxycarbonyl-L-phenylalanyl-L-methionate.

To 200 ml. of DMF was added 19.9 g. (0.1 mole) of the hydrochloride salt of methyl L-methionate. The mixture was cooled to 0° C., and 19.9 ml. (0.1 mole) of dicyclohexylamine was added to the stirred solution followed by 26.5 g. (0.1 mole) of $N^\alpha$-butyloxycarbonyl-L-phenylalanine, 13.5 g. (0.1 mole) of HBT, and 20.6 g. (0.1 mole) of DCC. The resulting mixture was stirred at 0° C. for two hours and then at room temperature for twenty-four hours. The mixture was re-cooled to 0° C., and the resulting precipitate was removed by filtration. The filtrate was concentrated in vacuo. The residue then was dissolved in ethyl acetate, and the ethyl acetate solution was washed successively with cold 0.75 N citric acid, water, 1 N sodium bicarbonate, and water. The ethyl acetate layer then was dried over magnesium sulfate and evaporated in vacuo to obtain a crystalline residue. The solid was recrystallized twice from ether-petroleum ether to afford 26.6 g. (65%) of the title compound, m.p. 89°–92° C.

Analysis, calculated for $C_{20}H_{30}N_2O_5S$ (410.53): C, 58,51; H, 7.37; N, 6.82. Found: C, 58.41; H, 7.15; N, 6.71.

B. $N^\alpha$-t-Butyloxycarbonyl-L-phenylalanyl-L-methionylamide.

To 60 ml. of methanol was added 13.0 g. (0.032 mole) of the compound from Part A. The resulting suspension was placed in a pressure bottle equipped with a magnetically driven stirring bar. The mixture was cooled to −78° C., and 60 ml. of anhydrous liquid ammonia were added. The reaction vessel was closed and was allowed to warm to room temperature. The mixture was stirred for twenty-four hours at room temperature. The vessel was slowly re-cooled to −78° C. and then was opened. The residual ammonia was evaporated by warming the mixture, and the product obtained after evaporation of the methanol was recrystallized from methanol to give 9.7 g. (77%) of the title compound, m.p. 192°–195° C.

Analysis, calculated for $C_{19}H_{29}N_3O_4S$ (395.52): C, 57.70; H, 7.39; N, 10.62. Found: C, 57.41; H, 7.17; N, 10.37.

C. L-Phenylalanyl-L-methionylamide Hydrochloride.

To 150 ml. of glacial acetic acid containing 10 ml. of anisole and 10 ml. of triethylsilane was added 9.6 g. (0.024 mole) of the product from Part B. Dry hydrogen chloride then was introduced through a gas dispersion tube. After thirty minutes, the reaction mixture was diluted with ether. The resulting precipitate was collected and was recrystallized from ethanol-ether to give 7.5 g. (94%) of the title compound, m.p. 214°–216° C.

Analysis, calculated for $C_{14}H_{22}N_3O_2SCl$ (331.87): C, 50.67; H, 6.68; N, 12.66. Found: C, 50.75; H, 6.84; N, 12.54.

D. $N^\alpha$-t-Butyloxycarbonyl-D-alanyl-glycyl-L-phenylalanyl-L-methionylamide.

To 40 ml. of DMF was added 1.66 g. (0.005 mole) the product from Part C. Dicyclohexylamine (0.99 ml.; 0.005 mole) was added, and the solution was stirred and cooled to 0° C. To the mixture then were added 0.88 g. (0.005 mole) of $N^\alpha$-t-butyloxycarbonyl-glycine followed by 0.68 g. (0.005 mole) of HBT and 1.03 g. (0.005 mole) of DCC. The resulting mixture was stirred for two hours at 0° C., and then at room temperature for twenty-four hours. After re-cooling the mixture to 0° C., the precipitate which formed was collected, and the filtrate was evaporated in vacuo. The resulting residue was dissolved in ethyl acetate, and the ethyl acetate solution was washed successively with 1 N sodium bicarbonate, water, cold 0.75 N citric acid and water. The organic phase was dried over magnesium sulfate, filtered, and evaporated in vacuo. The resulting residue then was dissolved in hot ethyl acetate. Upon cooling, a gel formed which could not be induced to crystallize. The gel was filtered, and the collected solid was dried to give 1.7 g. of amorphous solid. The solid was suspended in 50 ml. of acetonitrile containing 5 ml. of anisole and 5 ml. triethylsilane. p-Toluenesulfonic acid monohydrate was added, and the mixture was stirred for five hours. The resulting precipitate was collected by filtration and was dried to afford 1.6 g. (0.003 mole) of crude p-toluenesulfonate salt of glycyl-L-phenylalanyl-L-methionylamide. This impure product then was dissolved in 30 ml. of dry DMF. The mixture was cooled to 0° C., and 0.336 g. (0.003 mole) of DABCO was added followed, after ten minutes, by 0.8 g. (0.004 mole) of $N^\alpha$-t-butyloxycarbonyl-D-alanine, 0.540 g. (0.004 mole) of HBT, and 0.824 g. (0.004 mole) of DCC. The resulting mixture then was stirred at 0° C. for two hours and then at room temperature for forty-eight hours. The mixture was re-cooled to 0° C. and then was filtered. The filtrate then was evaporated in vacuo. The resulting residue was dissolved in n-butanol, and the n-butanol solution was washed successively with 1 N sodium bicarbonate, water, cold 0.75 N citric acid, and water. The organic phase was dried over magnesium sulfate, filtered, and concentrated in vacuo. The resulting residue was dissolved in hot ethanol and precipitated by addition of ethyl acetate to give 1.1 g. (42% overall) of the title compound.

Amino acid analysis, Found: Ala, 1.01; Gly, 1.01; Phe, 1.01; Met, 0.98.

E. $N^\alpha$-t-Butyloxycarbonyl-L-tyrosyl-D-alanyl-glycyl-L-phenylalanyl-L-methionylamide.

To a mixture of 20 ml. of glacial acetic acid, 2 ml. of anisole, and 2 ml. of triethylsilane were added 1.0 g. (0.0019 mole) of the product Part D. Anhydrous hydrogen chloride was introduced to the mixture via a gas dispersion tube for thirty minutes. Ether then was added to the reaction mixture, and a precipitate formed which was collected by filtration and dried (0.870 g.). The solid was dissolved in a mixture of 20 ml. of cold (0° C.) DMF and 0.38 ml. (0.0019 mole) of dicyclohexylamine. After ten minutes, 0.534 g. (0.0019 mole) of $N^\alpha$-t- butyloxycarbonyl-L-tyrosine, 0.257 g. (0.0019 mole) of HBT, and 0.391 g. (0.0019 mole) of DCC were added to the mixture. Stirring was continued for two hours at 0° C. and then for twenty-four hours at room temperature. After re-cooling the mixture to 0° C., the precipitate which formed was removed by filtration, and the filtration was concentrated in vacuo. The resulting residue then was dissolved in n-butanol, and the solution was washed successively with 1 N sodium bicarbonate, water, cold 0.75 N citric acid, and water. The organic phase then was dried over magnesium sulfate and filtered, and the filtrate was concentrated in vacuo. Attempts to crystallize the residue from ethyl acetate or from ethanol gave gels. The residue then was dissolved in hot methanol, and the solution was applied to a preparative thick layer chromatography plate and was eluted with chloroform-methanol (9:1). The product band was cut from the plate and wax extracted with chloroform-methanol. The solvent was evaporated in vacuo to give 0.270 g. (21%) of the title compound. $R_f{}^B = 0.17$.

Amino acid analysis, Found: Tyr, 1.00; Ala, 1.02; Gly, 0.99; Phe, 1.02; Met, 0.98.

F. L-Tyrosyl-D-alanyl-glycyl-L-phenylalanyl-L-methionylamide Hydrochloride.

To 5 ml. of glacial acetic acid containing 0.25 ml. of anisole was added 0.270 g. (0.0004 mole) of the product from Part E. Dry hydrogen chloride was introduced via a gas dispersion tube for twenty minutes. The resulting mixture then was frozen and lyophilized to give 0.182 g. (75%) of title compound. $R_f{}^A = 0.5$.

Amino acid analysis, Found: Tyr, 0.99; Ala, 1.00; Gly, 0.99; Phe, 1.01; Met, 0.91*.

*Analysis showed the presence of the methionine sulfoxide.

EXAMPLE 4

Preparation of
L-Tyrosyl-D-alanyl-glycyl-$N^\alpha$-methyl-L-phenylalanyl-$N^\alpha$-methyl-L-methionylamide A. N,N-dicyclohexylammonium $N^\alpha$-t-Butyloxycarbonyl-$N^\alpha$-methyl-L-phenylalinate.

To 80 ml. of dry THF was added 5.3 g. (0.02 mole) of $N^\alpha$-t-butyloxycarbonyl-L-phenylalanine. The resulting solution was cooled to about 10° C., and 10 ml. of dry DMF and 0.5 g. of 18-crown-6 ether were added. To the resulting mixture then was slowly added 10.15 g. (containing 0.060 mole of KH) of an oil dispersion of potassium hydride. Upon completion of the addition, the resulting mixture was cooled to 0° C., and 1.24 ml. (0.020 mole) of methyl iodide were added. Stirring was continued at room temperature for twentyl-four hours. The mixture then was poured onto crushed ice and was extracted with ether. The aqueous phase was acidified to pH 2 with citric acid then was extracted with ethyl acetate. The organic phase then was washed with water, dried over magnesium sulfate and concentrated in vacuo to give a syrup which would not crystallize. The nmr spectrum of the syrup was consistent with the expected derivative. nmr [$\delta$2.72, N—CH$_3$; $\delta$1.35, C(CH$_3$)$_3$]. The syrup was dissolved in ether, and 4.0 ml. of dicyclohexylamine was added. Crystals formed upon cooling. The precipitate was collected and was recrystallized from methanol-ether to give 6.8 g. (74%) of the title compound, m.p. 171°–174° C. $[\alpha]_D{}^{25} -22.0°$ (C=1, methanol).

Analysis, calculated for $C_{27}H_{44}N_2O_4$ (460.66): C, 70.40; H, 9.63; N, 6.08. Found: C, 70.60; H, 9.49; N, 6.19.

B. $N^\alpha$-t-Butyloxycarbonyl-$N^\alpha$-methyl-L-phenyl-alanyl-$N^\alpha$-methyl-L-methionylamide.

To solution of 30 ml. of dry DMF containing 1.98 g. (0.010 mole) of the hydrochloride salt of $N^\alpha$-methyl-L-methionylamide was added 4.16 g. (0.010 mole) of $N^\alpha$-t-butyloxycarbonyl-$N^\alpha$-methyl-L-phenylalanine. The resulting mixture was stirred for five minutes and then was cooled to 0° C. HBT (1.35 g.; 0.010 mole) of DCC (2.06 g.; 0.010 mole) were added. The resulting mixture was stirred for two hours at 0° C. and then for twnety-four hours at room temperature. The resulting precipitate was removed by filtration, and the filtrate was concentrated in vacuo to a syrup which was re-dissolved in ethyl acetate. The ethyl acetate solution was washed successively with 1 N sodium bicarbonate, water, cold 0.75 N citric acid, and water. The organic phase then was dried over magnesium sulfate and was concentrated in vacuo to a syrup. The resulting syrup was re-dissolved in chloroform and was applied to a 3×50 cm. column of silica gel (60–200 mesh) and was eluted with chloroform followed by chloroform-methanol (9.75:0.25). TLC analysis of the fractions from the column and subsequent combination on the basis of the TLC profile gave, after concentration in vacuo, 1.4 g. (33%) of a syrup exhibiting an nmr spectrum consistent for that of the title compound.

nmr: $\delta$2.93, N—CH$_3{}^{Phe}$; $\delta$2.73, N—CH$_3{}^{Met}$; $\delta$2.10, S—CH$_3$; $\delta$1.37, C(CH$_3$)$_3$.

C. $N^\alpha$-t-Butyloxycarbonyl-L-tyrosyl-D-alanyl-glycyl-$N^\alpha$-methyl-L-phenylalanyl-$N^\alpha$-methyl-l-methionylamide.

To a mixture of 5 ml. of glacial acetic acid, 1 ml. of anisole, and 1 ml. of triethylsilane was added 1.4 g. (0.0033 mole) of the product from Part B. Dry hydrogen chloride was introduced via a gas dispersion tube for thirty minutes, and the reaction mixture then was diluted with ether. The resulting precipitate was collected and dried (1.1 g.) and then was redissolved in 40 ml. of DMF. The reaction mixture then was cooled to 0° C., and 1.27 g. (0.0031 mole) of the product from Part E of Example 1, 0.420 g. (0.0031 mole) of HBT, and 0.640 g. (0.0031 mole) of DCC were added. After ten minutes, 0.43 ml. of (0.0031 mole) of triethylamine was added, and stirring was continued at 0° C. for two hours and then at 4° C. for forty-eight hours. The resulting precipitate was removed by filtration, and the filtrate was concentrated in vacuo to a syrupy residue which then was re-dissolved in ethyl acetate. The ethyl acetate solution was washed successively with 1 N sodium bicarbonate, water, cold 0.75 N citric acid, and water, and then was dried over magnesium sulfate, filtered, and concentrated in vacuo to give 2.0 g. of crude product. The product was dissolved in chloroform and was applied to 3×50 cm. column of silica gel (60–200 mesh) and eluted with chloroform followed by chloroform-methanol (9:1). TLC analysis of the fraction from the column and subsequent combination on the basis of the TLC profile gave, after concentration in vacuo, 1.1 g. (47%) of the non-crystalline title compound.

Analysis, calculated for $C_{35}H_{50}N_6O_8S$ (714.88): C, 58.80; H, 7.05; N, 11.76. Found: C, 59.01; H, 6.78; N, 11.58.

D. L-Tyrosyl-D-alanyl-glycyl-$N^\alpha$-methyl-L-phenylalanyl-$N^\alpha$-methyl-L-methionylamide.

To a mixture of 10 ml. of glacial acetic acid and 0.5 ml. of anisole was added 0.70 g. (0.001 mole) of the product from Part C. Dry hydrogen chloride was introduced via a gas dispersion tube for twenty minutes. The reaction mixture then was frozen and lyophilized to afford 0.678 g. of the hydroscopic title compound.

Analysis, calculated for $C_{30}H_{43}N_6O_6SCl.3H_2O$ (705.23): C, 51.08; H, 7.0; N, 11.91. Found: C, 51.13; H, 6.97; N, 11.72.

Amino acid analysis, Found: Tyr, 1.03; Ala, 1.01; Gly, 0.96.

EXAMPLE 5

Preparation of
L-Tyrosyl-D-alanyl-L-alanyl-L-phenylalanyl-$N^\alpha$-methyl-L-methionylamide 1.25 Hydrochloride Monoacetate A. Benzyl $N^\alpha$-t-Butyloxycarbonyl-O-benzyl-L-tyrosyl-D-alanyl-L-alinate.

To a solution of 3.19 g. (0.010 mole) of the p-toluenesulfonate salt of benzyl alinate in 30 ml. of dry DMF was added 4.43 g. (0.010 mole) of the product from Part B of Example 1. The resulting mixture was cooled to 0° C., and 1.12 g. (0.010 mole) of DABCO were added followed, in ten minutes, by 1.135 g. (0.010 mole) of HBT and 2.06 g. (0.010 mole) of DCC. The resulting mixture was stirred at 0° C. for two hours and then at room temperature for forty-eight hours. The resulting precipitate was removed by filtration, and the filtrate was evaporated in vacuo to a syrup. The syrup was re-dissolved in ethyl acetate, and the ethyl acetate solution was washed successively with 1 N sodium bicarbonate, water, cold 0.75 N hydrochloric acid, and water. The organic phase then was dried over magnesium sulfate and filtered, and the filtrate was concentrated in vacuo to give a residue which would not crystallize from ethanol or ether. Dilution of the ether solution was petroleum ether gave a gel which was collected by filtration and dried in vacuo. The impure amorphous solid (4.0 g.) was applied to a 3×50 cm. column of silica gel (60–200 mesh) and was eluted with chloroform followed by chloroform-methanol (9.75:0.25). TLC analysis of the fractions from the column, subsequent combination of the fractions on the basis of the TLC profile, and evaporation of the solvent in vacuo gave a syrupy residue. This material was dissolved in ether and was precipitated with petroleum ether to give 3.0 g. (50%) of the title compound as an amorphous solid, m.p. 100°–104° C.

Analysis, calculated for $C_{34}H_{41}N_3O_7$ (603.72): C, 67.64; H, 6.85; N, 6.96. Found: C, 67.56; H, 6.60; N, 7.16.

B. $N^\alpha$-t-Butyloxycarbonyl-L-tyrosyl-D-alanyl-L-alanine.

To 5 ml. of dry DMF was added 2.9 g. (0.0048 mole) of the product from Part A. To the mixture then was added 1.0 g. of 5% Pd/C followed by 50 ml. of ethanol. Hydrogen was introduced at atmospheric pressure and room temperature via a gas dispersion tube for six hours. The reaction vessel then was flushed with nitrogen, the catalyst was collected by filtration, and the filtrate was concentrated in vacuo. The residue was dissolved in ethyl acetate, and the solution was diluted with ether. The resulting precipitate was collected by filtration and dried in vacuo to give 1.5 g. (74%) of the title compound as an amorphous solid. $[\alpha]_D^{25}$ 25.9° (C=5, chloroform).

Analysis, calculated for $C_{20}H_{29}N_3O_7$ (423.47): C, 56.73; H, 6.90; N, 9.92. Found: C, 56.80; H, 6.95; N, 9.81.

C. $N^\alpha$-t-Butyloxycarbonyl-L-tyrosyl-D-alanyl-L-alanyl-L-phenylalanyl-$N^\alpha$-methyl-L-methionylamide.

To 10 ml. of dry DMF was added 0.692 g. (0.002 mole) of the hydrochloride salt of L-phenylalanyl-$N^\alpha$-methyl-L-methionylamide (prepared as in Part H of Example 1). The mixture was cooled to 0° C., and 0.28 ml. (0.002 mole) of triethylamine was added. The reaction mixture was stirred for ten minutes, and 0.846 g. (0.002 mole) of the product from Part B was added followed by 0.270 g. (0.002 mole) of HBT and 0.412 g. (0.002 mole) of DCC. The resulting mixture was stirred at 0° C. for two hours and then at room temperature for forty-eight hours. Upon re-cooling the mixture to 0° C., the mixture was filtered, and the filtrate was concentrated in vacuo. The residue was re-dissolved in ethyl acetate, and the ethyl acetate solution was washed successively with 1 N sodium bicarbonate, water, cold 0.75 N citric acid, and water. The organic phase then was dried over magnesium sulfate and filtered, and the filtrate was concentrated in vacuo to give 1.6 g. of crude product. The product was dissolved in chloroform and was applied to two preparative thick-layer chromatography plates. The plates were eluted with chloroform-methanol (9:1). The major band was cut from each plate, and the product was recovered from the silica gel by extraction with chloroform-methanol. The eluate (1.3 g.) was dissolved and reapplied to a single thick-layer chromatography plate and re-chromatographed to give 1.0 g. (70%) of the title compound as an amorphous solid; $[\alpha]_D^{25}$ −25.6° (C=0.5, MeOH).

Analysis, calculated for $C_{35}H_{50}N_6O_8S$ (714.88): C, 58.80; H, 7.05; N, 11.76. Found: C, 58.60; H, 6.87; N, 11.53.

D. L-Tyrosyl-D-alanyl-L-alanyl-L-phenylalanyl-$N^\alpha$-methyl-L-methionylamide Hydrochloride Monoacetate.

To 5 ml. of glacial acetic acid containing 0.5 ml. of anisole was added 0.880 g. (0.0011 mole) of the product from Part C. Dry hydrogen chloride was introduced via a gas dispersion tube for twenty minutes. The reaction mixture then was frozen and lyophilized to afford 0.704 g. of the title compound. $[\alpha]_D^{25}$ −16.2 (C=0.5, MeOH).

Analysis, calculated for $C_{30}H_{42}N_6O_6S.1.25HCl.C_2H_4O_2$ (719.14): C, 53.43; H, 6.45; N, 11.68; Cl, 6.16. Found: C, 53.48; H, 6.47; N, 11.62; Cl, 6.50.

Amino acid analysis, Found: Tyr, 1.00; Ala, 1.99; Phe, 1.01.

EXAMPLE 6

Preparation of
L-Tyrosyl-D-alanyl-glycyl-L-phenylalanyl-L-$N^\alpha$-methyl-S-ethyl-cysteinylamide acetate A. $N^\alpha$-t-Butyloxycarbonyl-s-ethyl-L-cysteine, Dicyclohexylamine Salt, To 400 ml. of N,N-dimethylformamide (DMF) were added 50 grams (0.336 mole) of L-(S-ethyl)cysteine. Tetramethylguanidine (44.8 ml.; 0.336 mole) and dicyclohexylamine (66.8 ml.; 0.336 mole) were added to the reaction mixture. t-Butyl azidoformate (68 ml.; 0.50 mole) then was added dropwise to the reaction mixture over a one hour period, and the mixture was stirred for 48 hours at room temperature. The precipitated dicyclohexylammonium azide was removed by filtration, and the filtrate was evaporated in vacuo. The residue was partitioned between ether and water. The pH of the aqueous layer was adjusted to 8.0. The organic layer was separated and discarded. The aqueous layer then was acidified to pH 2.0 with cold dilute hydrochloric acid and was extracted with cold ethyl acetate. The ethyl acetate phase then was washed with water, dried over magnesium sulfate, and concentrated in vacuo.

The resulting residue was dissolved in ether, and 66.8 ml. (0.336 mole) of dicyclohexylamine were added. The resulting percipitate was collected and recrystallized from ethyl acetate to afford 32.8 grams (23% theory) of the title compound, m.p. 156°–159° C.; $[\alpha]_D^{25}$ −1.1° (C=1, MeOH); $[\alpha]_{365}^{25}$ −7.7° (C=1, MeOH).

Analysis, calculated for $C_{22}H_{42}N_2O_4S$ (430.6): C, 61.36; H, 9.83; N, 6.51. Found: C, 61.37; H, 9.98; N, 6.26.

B. $N^\alpha$-Butyloxycarbonyl-N-methyl-S-ethyl-L-cysteinylamide.

To 50 ml. of dry tetrahydrofuran (THF) were added 18.58 grams (74.3 mmoles) of $N^\alpha$-butyloxycarbonyl-S-ethyl-L-cysteine (prepared by neutralization of the product from Part A and extraction into ethyl acetate). The resulting mixture was added dropwise over 30 minutes to a mechanically stirred suspension of 42.45 grams of a potassium hydride suspension (22.1% KH in mineral oil; 0.234 mole KH) in 375 ml. of THF at 0° C. and containing 0.35 gram of 18-crown-6 ether. Methyl iodide (9.25 ml.; 0.149 mole) in 20 ml. of THF was added dropwise over 15–20 minutes. The mixture was stirred at 0° C. for 1.5 hours, and 7.5 ml. of acetic acid in 7.5 ml. of THF were added dropwise followed by 5 ml. of ethanol. The resulting reaction mixture then was poured onto ice, and the pH of the mixture was adjusted to about 9 by addition of 2 N sodium hydroxide. The resulting aqueous solution was extracted with ether. The pH of the aqueous layer then was adjusted to 3 by addition of solid citric acid and then was re-extracted with three 300 ml. portions of ether. The ether extracts were combined, back extracted with water, dried over magnesium sulfate, and concentrated in vacuo. The resulting residue was dissolved in 200 ml. of ether, and 9.56 ml. (74.3 mmole) of d(+) α-methylbenzylamine were added. The mixture was cooled, and 500 ml. of petroleum ether were added. No crystallization occurred; the solution was concentrated in vacuo and was redissolved in petroleum ether. The mixture was cooled to −78° C., and a small amount of precipitate formed which was collected by filtration (2.74 grams). The mother liquor was concentrated in vacuo, and the residue was redissolved in ether. The ether solution was extracted with 1 N citric acid. The organic layer was back extracted with water, dried over magnesium sulfate and concentrated in vacuo to provide 6.56 grams (33% theory) of a syrup. $[\alpha]_D^{25}$ −61.1°, (C=1, EtOH); NMR (CDCl$_3$) δ2.90, N—CH$_3$; δ1.45, t-Bu; δ4.9–4.5, CH.

The product (6.5 grams; 0.025 mole) was dissolved in 80 ml. of DMF, and the mixture was cooled to −15° C. Isobutyl chloroformate (3.6 ml.; 0.027 mole) was added followed by N-methylmorpholine (2.99 ml.; 0.027 mole). The resulting mixture was stirred for 10 minutes at −15° C., and then anhydrous ammonia was bubbled into the reaction mixture for one hour. The mixture was stirred an additional 4 hours at −15° C. and then was poured onto a mixture of ice and 1 N sodium bicarbonate. The cold aqueous layer was extracted with ether. The ether extract then was extracted with cold 0.75 N citric acid and water, dried over magnesium sulfate, and concentrated in vacuo to give a residue which was crystallized from a mixture of ether and petroleum ether to give 1.7 grams (26%) of the title compound, m.p. 56°–59° C. $[\alpha]_D^{25}$ −127.6 (C=0.5, CHCl$_3$); NMR (CHCl$_3$) δ2.80, N—CH$_3$; δ1.46, t-Bu; δ4.9–4.5, α—CH.

Analysis, calculated for $C_{11}H_{21}N_2O_3S$ (261.36): C, 50.55; H, 8.10; N, 10.72. Found: C, 50.56; H, 7.93; N, 10.51.

C. $N^\alpha$-t-Butyloxycarbonyl-L-phenylalanyl-$N^\alpha$-methyl-S-ethyl-L-cysteinylamide.

To 20 ml. of glacial acetic acid containing 1 ml. of triethylsilane and 4 ml. of anisole were added 2.5 grams (9.5 mmoles) of $N^\alpha$-t-butyloxycarbonyl-$N^\alpha$-methyl-S-ethyl-L-cysteinylamide. Dry hydrogen chloride was bubbled into the mixture for 30 minutes, and ether then was added to precipitate the hydrochloride salt (1.8 grams). The precipitate was dissolved in 25 ml. of DMF. The mixture was cooled to 0° C. and was neutralized with 1.31 ml. of triethylamine. $N^\alpha$-t-Butyloxycarbonyl-L-phenylalanine (2.65 grams; 0.01 mole) was added followed by 1.35 grams (0.01 mole) of HBT and 2.06 grams (0.01 mole) of DCC. The resulting mixture was stirred at 0° C. for two hours and then at room temperature for 24 hours. The mixture was cooled to 0° C., and the resulting precipitate was removed by filtration. The filtrate was concentrated in vacuo to a residue. The residue was dissolved in ethyl acetate, and the ethyl acetate solution was extracted with 1 N sodium bicarbonate, water, 0.75 N citric acid, and water. The mixture then was dried over magnesium sulfate, and the solvent was removed in vacuo to give a syrup. The syrup was dissolved in chloroform, and the solution was applied to a 3×45 cm. column containing Grade 62 Grace and Davidson silica gel. Elution with a chloroform-methanol step gradient [CHCl$_3$→CHCl$_3$/MeOH (9:1)] and location of the product by TLC profile of the fractions gave, after combining the proper fractions and evaporation in vacuo of solvent, 3.0 grams of the title compound. $[\alpha]_D^{25}$ −77° (C=0.5, MeOH).

Analysis, calculated for $C_{20}H_{31}N_3O_4S$ (409.5): C, 58.65; H, 7.63; N, 10.26. Found: C, 58.87; H, 7.41; N, 9.81.

D. $N^\alpha$-t-Butyloxycarbonyl-L-tyrosyl-D-alanyl-glycine, Dicyclohexylamine Salt.

The product from hydrogenolysis (according to the method of Part E of Example 1) of 46.80 g. of benzyl $N^\alpha$-t-butyloxycarbonyl-O-benzyl-L-tyrosyl-D-alanyl-glycinate was dissolved in 150 ml. of isopropyl alcohol, and 16 ml (0.081 mole) of dicyclohexylamine were added. Ether was added to bring the volume to about 1.5 liters. The semi-solid mass was triturated until solid, and the resulting precipitate was collected and dried to give 46.04 g. (98%), m.p. 194.5°–197° C. The solid was dissolved in 100 ml. of boiling methanol, and 500 ml. of isopropyl alcohol were added. The volume of the solution was reduced under a nitrogen stream to about 150 ml. Upon cooling, crystallization began. The mixture was allowed to stand overnight, and the precipitate was collected and dried to give 41.44 g. (88%) of the title compound, m.p. 198°–200.5° C. $[\alpha]_D^{25}$ +17.9° (C=1, MeOH).

Analysis, calculated for $C_{31}H_{50}N_4O_7$ (590.8): C, 63.03; H, 8.53; N, 9.48. Found: C, 62,95; H, 8.77; N, 9.20.

E. $N^\alpha$-t-Butyloxycarbonyl-L-tyrosyl-D-alanyl-glycyl-L-phenylalanyl-$N^\alpha$-methyl-S-ethyl-L-cysteinylamide.

To 20 ml. of glacial acetic acid containing 3 ml. of anisole and 3 ml. of triethylsilane were added 2.5 grams (6.1 mmoles) of the product from Part C. Dry hydrogen chloride gas was bubbled into the reaction mixture for 25 minutes. Ether then was added, and the mixture was cooled and filtered to afford 1.9 grams (5.5 mmoles) of the hydrochloride salt. The salt was dissolved in 25 ml. of DMF. The mixture was cooled, and 3.2 grams (5.5 mmoles) of $N^\alpha$-t-butyloxycarbonyl-L-tyrosyl-D-alanyl-glycine, dicyclohexylamine salt, were added. The resulting mixture was stirred at 0° C. for 10 minutes. HBT (0.74 grams; 5.5 mmoles) and DCC (1.1 grams; 5.5 mmoles) were added, and the reaction mixture was stirred at 0° C. for two hours and at 4° C. for 48 hours. The resulting precipitate was removed by filtration, and the filtrate was evaporated in vacuo. The residue was dissolved in ethyl acetate, and the ethyl acetate solution was extracted with 1 N sodium bicarbonate, water, 0.75 N citric acid, and water. The organic phase was dried over magnesium sulfate and was evaporated in vacuo to give 3.5 grams of the crude title compound. The product was dissolved in chloroform and was applied to a 3×45 cm. column of Grade 62 Grace and Davidson silica gel and was eluted with a step gradient of chloroform-methanol [CHCl$_3$→CHCl$_3$/MeOH (9:1)]. Fractions were combined on the basis of the TLC profile and were evaporated in vacuo to give 2.4 grams (62%) of pure title compound. $[\alpha]_D^{25}$ −30.7° (C=0.5, MeOH).

Analysis, calculated for C$_{34}$H$_{48}$N$_6$O$_8$S (700.86): C, 58.27; H, 6.90; N, 11.99. Found: C, 58.14; H, 6.98; N, 11.94.

Amino acid analysis, found: Tyr, 1.01; Ala, 1.00; Gly, 1.00; Phe, 0.98; NH$_3$, 1.09.

F. L-Tyrosyl-D-alanyl-glycyl-L-phenylalanyl-L-N$^\alpha$-methyl-S-ethyl-cysteinylamide acetate.

To 20 ml. of glacial acetic acid containing 2 ml. of anisole and 2 ml. of triethylsilane was added 2.2 grams (3 mmoles) of the product from Part E. Dry hydrogen chloride was bubbled into the reaction mixture for 25 minutes. Ether then was added to the mixture, and the mixture was cooled. The resulting precipitate was filtered and dried (2.0 grams). A portion of the precipitate (1.2 grams) was dissolved in sufficient buffer (1% pyridine and 0.05% acetic acid in water) to provide a total of 10 ml. The solution was applied to a 2.5×99 cm. column of DEAE-Sephadex A 25 (acetate) previously equilibrated with the same buffer. The eluate was monitored at 280 nm, and the appropriate fractions were combined and lyophilized. Relyophilization from 10% acetic acid followed by lyophilization from a 75:25 mixture of water and acetonitrile gave 0.59 gram of the title compound. $[\alpha]_D^{25}$ +9.9 (C=0.5, 1 N HCl).

Analysis, calculated for C$_{31}$H$_{44}$N$_6$O$_8$S (660.79): C, 56.35; H, 6.71; N, 12.72; S, 4.85. Found: C, 56.63; H, 6.72; N, 12.63; S, 4.69.

Amino acid analysis, Found: Tyr, 1.00; Ala, 1.01; Gly, 1.00; Phe, 0.98; NH$_3$, 1.09.

EXAMPLE 7

Preparation of L-Tyrosyl-D-alanyl-glycyl-L-phenylalanyl-N$^\alpha$-methyl-L-leucylamide A. N$^\alpha$-t-Butyloxycarbonyl-N$^\alpha$-methyl-L-leucine, d(+)α-Methylbenzylamine Salt.

To 20 ml. of ether were added 12.5 grams (0.05 mole) of N$^{60}$-t-butyloxycarbonyl-L-Leucine hydrate. The mixture was dried over magnesium sulfate and concentrated in vacuo. The residue was dissolved in 75 ml. of THF, and the resulting solution was added dropwise over a 35 minute period to a mechanically stirred, cooled (0° C.) suspension of 27.9 grams of a potassium hydride suspension (22.1% suspension in mineral oil; 0.154 mole KH) in 200 ml. of THF containing 0.25 gram of 18-crown-6 ether. Methyl iodide (6.4 ml.) in 10 ml. of THF then was added dropwise over a 15 minute period. The mixture was maintained at 0° C. for 3 hours, and 5 ml. of acetic acid in 5 ml. of THF then were added dropwise followed by 5 ml. of ethanol. The resulting mixture was poured onto 500 ml. of ice, and the pH of the mixture was adjusted to about 9 by addition of 1 N sodium hydroxide. The aqueous solution was extracted with ether and then was acidified to pH 3 by addition of solid citric acid. The acidified aqueous suspension then was extracted with ether. The combined ether extracts were washed with water, dried over magnesium sulfate, and concentrated in vacuo to give 13.2 grams (107% theory) of crude product. Examination of the product by TLC indicated the presence of some unreacted starting material. The product was dissolved in ether, and 5.25 ml. (0.05 mole) of t-butylamine were added. The ether solution was diluted with petroleum ether and cooled overnight. A precipitate (5.4 grams) formed and was removed. The filtrate was extracted with 1 N citric acid and then with water. The organic phase was dried over magnesium sulfate and concentrated in vacuo to a residue. The residue (6.45 grams) was dissolved in 100 ml. of ether, and 3.39 grams (0.026 mole) of d(+)α-methylbenzylamine were added. The solution was cooled overnight and then was filtered to afford 9.09 grams (49% theory overall) of the title compound, m.p. 120°–122° C. $[\alpha]_D^{25}$ −14.1° (C=1, MeOH).

Analysis, calculated for C$_{20}$H$_{34}$N$_2$O$_4$ (366.5): C, 65.54; H, 9.35; N, 7.64. Found: C, 65.83; H, 9.05; N, 7.35.

B. N$^\alpha$-t-Butyloxycarbonyl-N$^\alpha$-methyl-L-leucylamide.

To 80 ml. of DMF were added 11.5 grams (0.047 mole) of N$^\alpha$-t-butyloxycarbonyl-N$^\alpha$-methyl-L-Leucine (prepared by neutralization of the product from Part A with citric acid and extraction into ether). The mixture was cooled to −15° C. Isobutyl chloroformate (6.7 ml.; 0.052 mole) and N-methylmorpholine (5.7 ml.; 0.052 mole) were added. The mixture was stirred for 10 minutes at −15° C., and anhydrous ammonia was bubbled into the reaction mixture for one hour. Stirring then was continued for 4 hours at −15° C. The reaction mixture was poured onto a mixture of 1 N sodium bicarbonate and ice. The cold mixture was extracted with ether. The ether layer then was extracted with 0.75 N citric acid and water, dried over magnesium sulfate, and evaporated in vacuo. The residue was crystallized from a mixture of ether and petroleum ether to give 5.5 grams (48%) of the title compound, m.p. 127°–128° C. $[\alpha]_D^{25}$ −42.2° )C=1, MeOH).

Analysis, calculated for C$_{12}$H$_{24}$N$_2$O$_3$ (244.3): C, 58.99; H, 9.90; N, 11.47. Found: C, 59.17; H, 9.66; N, 11.21.

C. N$^\alpha$-t-Butyloxycarbonyl-L-phenylalanyl-N$^\alpha$-methyl-L-leucylamide.

To 30 ml. of glacial acetic acid containing 3 ml. of anisole and 3 ml. of triethylsilane were added 5.0 grams (0.02 mole) of the product from Part B. Dry hydrogen chloride was bubbled into the reaction mixture for 25 minutes. Ether then was added, and the mixture was cooled. The resulting precipitate was collected and dried (3.6 grams). The collected hydrochloride salt was dissolved in 60 ml. of DMF. The resulting solution was cooled to 0° C., and 3.99 ml. (0.02 mole) of dicyclohexylamine were added. The mixture was stirred at 0° C. for 10 minutes, and 5.3 grams (0.02 mole) of N$^\alpha$-t-butyloxycarbonyl-L-phenylalanine were added followed by 2.7 grams (0.02 mole) of HBT and 4.12 grams (0.02 mole) of DCC. The reaction mixture was stirred for 2 hours at 0° C. and then at room temperature for 24 hours. The mixture was cooled to 0° C. and filtered, and the filtrate was evaporated in vacuo. The residue was dissolved in ethyl acetate, and the ethyl acetate solution was extracted with 1 N sodium bicarbonate, water, 0.75

N citric acid, and water. The solution then was dried over magnesium sulfate, and the solvent was evaporated in vacuo. The resulting residue was dissolved in chloroform and applied to a 3×45 cm column of Grade 62 Grace and Davidson silica gel. Elution was effected with a chloroform-methanol step gradient [CHCl$_3$→CHCl$_3$/MeOH (9:1)]. Fractions were combined on the basis of the TLC profile to give, after evaporation of solvent, 5.7 grams (73%) of the title compound. $[\alpha]_D^{25}$ −49.5° (C=0.5, MeOH); NMR (CDCl$_3$) δ1.4, t-Bu; δ7.25, phenyl; δ0.95–0.75, CH(CH$_3$)$_2$; δ2.7, N—CH$_3$.

D. N$^\alpha$-t-Butyloxycarbonyl-L-tyrosyl-D-alanyl-glycyl-L-phenylalanyl-N$^\alpha$-methyl-L-leucylamide.

To a mixture of 20 ml. of 1 N HCl in glacial acetic acid containing 1 ml. of anisole were added 2.0 grams of the product from Part C. The mixture was maintained at room temperature for 30 minutes, and ether then was added. The mixture was cooled, and the resulting precipitate was collected and dried (1.63 grams). The collected hydrochloride salt was dissolved in 30 ml. of DMF, and 2.95 grams (0.05 mole) of N$^\alpha$-t-butyloxycarbonyl-L-tyrosyl-D-alanyl-glycine, dicyclpohexylamine salt were added. The mixture was stirred for 15 minutes at 0° C., and 0.675 grams (0.005 mole) of HBT and 1.3 grams (0.005 mole) of DCC were added. The reaction mixture then was stirred for 24 hours at 4° C. The resulting precipitate was collected, and the filtrate was concentrated in vacuo. The residue was dissolved in ethyl acetate, and the ethyl acetate solution was extracted with 1 N sodium bicarbonate, water, 0.75 N citric acid, and water. The ethyl acetate solution then was dried over magnesium sulfate and was concentrated in vacuo. The resulting residue was dissolved in chloroform, and the chloroform solution was applied to a 3×45 cm. column of Woelm Grade III silica gel. The column was eluted with a chloroform-methanol step gradient [CHCl$_3$→CHCl$_3$—MeOH (9:1)], and fractions were combined on the basis of the TLC profile. After evaporation of solvent, 2.3 grams (67%) of the title compound were obtained. $[\alpha]_D^{25}$ −17.5° (C=0.6, MeOH).

Analysis, calculated for C$_{35}$H$_{50}$N$_6$O$_8$ (682.8): C, 61.57; H, 7.38; N, 12.31. Found: C, 61.33; H, 7.47; N, 12.08.

Amino acid anaylsis, found: Tyr, 1.00; Ala, 1.01; Gly, 0.99; Phe, 1.00; NH$_3$, 1.08.

E. L-Tyrosyl-D-alanyl-glycyl-L-phenylalanyl-N$^\alpha$-methyl-L-leucylamide.

To 5 ml. of formic acid containing 0.5 ml. of anisole and 0.1 ml. of triethylsilane were added 1.8 grams (0.003 mole) of the product from Part D. The mixture was stirred at room temperature for 3 hours. The reaction mixture then was diluted with ether and was allowed to stand for one hour. The ether was decanted from the resulting oil, and the oil was dissolved in ethanol. Addition of ether produced a precipitate which was filtered and dried to give 0.9 gram of crude title compound. The product was dissolved in sufficient buffer (1% pyridine and 0.05% formic acid in water) to make a total of 5.0 ml. The solution was applied to a 2.5×100 cm. column of DEAE-Sephadex A-25 (formate) and was eluted with the same buffer. The appropriate fractions were combined on the basis of the UV elution profile (280 nm) and lyophilized. Re-lyophilization from 10% acetic acid and from a 75:25 mixture of water and acetonitrile afforded 0.852 gram of the title compound. $[\alpha]_D^{25}$ +23.2 (C=0.6 1 N HCl).

Amino acid analysis, found: Tyr, 1.02; Ala, 1.00; Gly, 1.01; Phe, 0.96; NH$_3$, 1.03.

EXAMPLE 8

Preparation of
L-Tyrosyl-D-alanyl-glycyl-L-phenylalanyl-S-p-methoxybenzyl-L-cysteinylamide Hydrochloride A. N$^{60}$-t-Butyloxycarbonyl-S-p-methoxybenzyl-L-cysteinylamide.

To 80 ml. of DMF cooled to −15° C. were added 6.82 grams (0.02 mole) of N$^\alpha$-t-butyloxycarbonyl-S-p-methoxybenzyl-L-cysteine. To the resulting cooled mixture were added 2.88 ml. (0.022 mole) of isobutyl chloroformate and 2.42 ml. (0.022 mole) of N-methylmorpholine. After 10 minutes, anhydrous ammonia was bubbled into the reaction mixture for 1.5 hours. Stirring then was continued at −15° C. for an additional 2 hours. The reaction mixture was poured into a mixture of ice and 1 N sodium bicarbonate. The resulting aqueous suspension was extracted with ethyl acetate, and the ethyl acetate extract was washed with water, 0.75 N citric acid, and water. The organic layer then was dried over magnesium sulfate and concentrated in vacuo. The resulting residue was recrystallized from a mixture of ethanol and water to afford 4.9 grams (72%) of the title compound, m.p. 138°-140° C. $[\alpha]_D^{25}$ −12.8° (C=5, MeOH).

Analysis, calculated for C$_{16}$H$_{24}$N$_2$O$_4$S (340.4): C, 56.45; H, 7.11; N, 8.23. Found: C, 56.58; H, 6.97; N, 8.07.

B. N$^\alpha$-t-Butyloxycarbonyl-L-phenylalanyl-S-p-methoxybenzyl-L-cysteinylamide.

Anhydrous hydrogen chloride was bubbled into a solution of 4.1 grams (0.012 mole) of the product from Part A in 45 ml. of glacial acetic acid, 5 ml. of anisole, and 5 ml. of triethylsilane. After 20 minutes, ether was added, and the resulting precipitate was collected and dried (3.3 grams). The collected hydrochloride salt was dissolved in 50 ml. of DMF, and 2.92 grams (0.012 mole) of dicyclohexylamine, 3.19 grams (0.012 mole) of N$^\alpha$-t-butyloxycarbonyl-L-phenylalanine, and 1.62 grams (0.012 mole) of HBT were added. The mixture was stirred for 10 minutes at 0° C., and 2.47 grams (0.012 mole) of DCC were added. After 2 hours at 0° C., the reaction mixture was stirred at room temperature for 24 hours and then was re-cooled to 0° C. The resulting precipitate was filtered. The filtrate was concentrated in vacuo, and the resulting residue was dissolved in n-butyl alcohol. The solution was extracted with 1 N sodium bicarbonate and water and then was dried over magnesium sulfate and evaporated in vacuo. The resulting residue was recrystallized from ethanol to afford 4.95 grams (85%) of the title compound, m.p. 175°-178° C. $[\alpha]_D^{25}$ −35.1 (C=0.5, DMF).

Analysis, calculated for C$_{25}$H$_{33}$N$_3$O$_5$S (487.6): C, 61,58; H, 6.82; N, 8.62. Found: C, 61.78; H, 6.78; N, 8.28.

C. N$^\alpha$-t-Butyloxycarbonyl-L-tyrosyl-D-alanyl-glycyl-L-phenylalanyl-S-p-methoxybenzyl-L-cysteinylamide.

Anhydrous hydrogen chloride was bubbled into a solution of 1.3 grams (0.027 mole) of the product from Part B in 40 ml. of glacial acetic acid, 4 ml. of anisole, and 4 ml. of triethylsilane. After 20 minutes, ether was added to the mixture, and the resulting precipitate was collected and dried (1.1 gram). The collected hydrochloride salt was dissolved in 10 ml. of DMF, and the mixture was cooled to 0° C. Triethylamine (0.34 ml.; 0.0026 mole) was added. After 10 minutes, 1.06 grams (0.0026 mole) of N$^\alpha$-t-butyloxycarbonyl-L-tyrosyl-L- alanyl-glycine was added followed by 0.35 gram (0.0026 mole) of HBT and 0.536 grams (0.0026 mole) of DCC. The resulting reaction mixture was stirred at 0° C. for 2 hours and then at 4° C. for 72 hours. The resulting precipitate was collected, and the filtrate was concentrated in vacuo. The residue was dissolved in ethyl acetate, and the ethyl acetate solution was extracted with 1 N sodium bicarbonate, water, 0.75 N citric acid, and water. The extract then was dried over magnesium sulfate and concentrated in vacuo. The resulting residue was dissolved in ethyl acetate and purified by dry column chromatography on Grace and Davidson Grade 62 silica gel. Fractions were combined on the basis of the TLC profile and concentrated to give 1.1 grams (52%) of the title compound by crystallization from a small volume of ethyl acetate. $[\alpha]_D^{25}$ −4.3 (C=0.5, DMSO).

Analysis, calculated for $C_{39}H_{50}N_6O_9S$ (778.9): C, 60.14; H, 6.47; N, 10.79. Found: C, 59.95; H, 6.24; N, 10.53.

Amino acid analysis, found: Tyr, 0.98; Ala, 1.03; Gly, 1.01; Phe, 0.98; $NH_3$, 0.99.

D. L-Tyrosyl-D-alanyl-glycyl-L-phenylalanyl-S-p-methoxybenzyl-L-cysteinylamide Hydrochloride.

To 20 ml. of glacial acetic acid containing 0.5 ml. of anisole were added 0.90 grams (0.0012 mole) of the product from Part C. Dry hydrogen chloride was bubbled into the mixture for 30 minutes. The mixture then was lyophylized to give 0.862 grams (100%) of the title compound. $[\alpha]_D^{25}$ +2.6 (C=0.5, 1 N HCl).

Analysis, calculated for $C_{34}H_{43}N_6O_7S$ (715.2): C, 57.09; H, 6.06; N, 11.75; Cl, 4.96. Found: C, 56.85; H, 6.06; N, 11.48; Cl, 5.21.

Amino acid analysis, found: Tyr, 0.99; Ala, 1.01; Gly, 1.01; Phe, 0.98; $NH_3$, 0.99.

EXAMPLE 9

Preparation of L-Tyrosyl-D-alanyl-glycyl-L-phenylalanyl-$N^\alpha$-methyl-L-methionylamide Acetate A. $N^\alpha$-t-Butyloxycarbonyl-$N^\alpha$-methyl-L-methionine, d(+)α-methylbenzlamine salt.

The dicyclohexyalamine salt of $N^\alpha$-t-butyloxycarbonyl-L-methoionine (86.13 g.; 0.2 mole) was suspended in 600 ml. of cold ether. The suspension was extracted four times with 100 ml. of cold 1.5 N citric acid and water. The resulting organic phase was separated, dried over magnesium sulfate, and concentrated in vacuo. The residue was dissolved in 150 ml. of THF, and the solution was added dropwise over 30 minutes to a mechanically stirred suspension of 0.6 mole of potassium hydride in 1000 ml. of dry THF (0° C.) containing 1.0 g. of 18-crown-6 ether. Methyl iodide (25 ml.; 0.4 mole) was added dropwise over a 15 minute period. Two hours after addition of the methyl iodide, a mixture of 20 ml. of acetic acid and 20 ml. of THF was added dropwise, followed by 40 ml. of ethanol. The mixture was stirred for 30 minutes and then was poured onto two liters of ice. The pH of the aqueous mixture was adjusted to 7 with 2 N potassium hydroxide. The aqueous mixture was extracted three times with 400 ml. of ether and then was acidified to pH 3 with solid citric acid. The mixture was extracted three times with 500 ml. of ether. The ether extracts were combined, extracted, dried over magnesium sulfate, and evaporated in vacuo to a syrup (44.76 g.; 84% theory). The syrup was dissolved in 450 ml. of ethyl acetate, and 25.78 ml. (0.2 mole) of d(+)α-methylbenzylamine were added. Upon cooling and scratching, crystallization ensued. The title compound was collected by filtration to give 51.05 g. (66%), m.p. 131°–134° C. $[\alpha]_D^{25}$ −18.9° (C=1, EtOH).

Analysis, calculated for $C_{19}H_{32}N_2O_4S$ (384.54): C, 59.35; H, 8.39; N, 7.29. Found: C, 59.15; H, 8.12; N, 7.21.

B. $N^\alpha$-t-Butyloxycarbonyl-$N^\alpha$-methyl-L-methionylamide.

$N^\alpha$-t-Butyloxycarbonyl-$N^\alpha$-methyl-L-methionine (33.3 g.; 0.127 mole; prepared by acidification of the d(+)α-methylbenzylamine salt from Part A and extraction into ether) was dissolved in 160 ml. of DMF. The solution was cooled to −15° C., and 18.3 ml. (0.14 mole) of isobutyl chloroformate and 15.4 ml. (0.14 mole) of N-methylmorpholine were added. The mixture was stirred for 10 minutes at −15° C., and anhydrous ammonia was bubbled into the mixture via a gas dispersion tube for one hour. The reaction mixture stirred for four hours at −15° C. and then was poured into 300 ml. of cold 1 N $NaHCO_3$ solution. The aqueous suspension was extracted with ether. The ether extract was washed with water, cold 0.75 N citric acid, and water, dried over $MgSO_4$, and evaporated in vacuo to a syrup. The syrup was recrystallized from ether-petroleum ether to 16 g. (48%) of the title compound, m.p. 75°–77° C. $[\alpha]_D^{25}$ −117.3° (C=0.5, $CHCl_3$).

Analysis, calculated for $C_{11}H_{22}N_2SO_3$ (262.37): C, 50.36; H, 8.45; N, 10.68. Found: C, 50.63; H, 8.57; N, 10.45.

C. $N^\alpha$-t-Butyloxycarbonyl-L-phenylalanyl-$N^\alpha$-methyl-L-methionylamide.

A mixture of 70 ml. of glacial acetic acid, 5 ml. of anisole, 7 ml. of triethylsilane, and 13.15 g. (0.05 mole) of the product from Part B was prepared. Anhydrous hydrogen chloride was bubbled into the resulting mixture for 25 minutes. The mixture then was poured into ether, and the resulting precipitate was collected and dried (9.9 g.). The hydrochloride was dissolved in 200 ml. of DMF. The mixture was cooled to 0° C., and 9.9 ml. (0.05 mole) of dicyclohexylamine were added. After stirring for 10 minutes, 6.8 g. (0.05 mole) of HBT, 13.3 g. (0.05 mole) of $N^\alpha$-t-butyloxycarbonyl-L-phenylalanine, and 10.3 g. (0.05 mole) of DCC were added. The resulting mixture was stirred for two hours at 0° C., and then for 48 hours at room temperature. The mixture was cooled at 0° C. and filtered. The resulting filtrate then was concentrated in vacuo to an oil. The oil was redissolved in ethyl acetate, and the solution was washed successively with 1 N sodium bicarbonate, water, 0.75 N citric acid, and water. The ethyl acetate solution then was dried over magnesium sulfate and evaporated in vacuo to provide a residue which crystallized from ether to afford 16.4 g. (80%) of the title compound, m.p. 114°–115° C. $[\alpha]_D^{25}$ −43.4° (C=0.5, MeOH).

Analysis, calculated for $C_{20}H_{31}N_3O_4S$ (409.55): C, 58.65; H, 7.63; N, 10.26. Found: C, 58.76; H, 7.42; N, 10.30.

D. $N^\alpha$-t-Butyloxycarbonyl-L-tyrosyl-D-alanyl-glycyl-L-phenylalanyl-$N^\alpha$-methyl-L-methionylamide.

To a mixture of 20 ml. of glacial acetic acid, 2 ml. of anisole, and 2 ml. of triethylsilane were added 3.5 g. (8.56 mmoles) of the product from Part C. Dry hydrogen chloride was bubbled into the mixture for 25 minutes. Ether was added to the mixture, and the hydrochloride precipitated and was filtered and dried in vacuo. A solution of 5.0 g. (8.47 mmoles) of $N^\alpha$-t-butyloxycarbonyl-L-tyrosyl-D-alanyl-glycine, dicyclohexylamine salt, in 40 ml. of DMF was cooled to 0°

C., and the above hydrochloride salt was added. After stirring at 0° C. for a few minutes, 1.1 g. (8.47 mmoles) of HBT and 1.7 g. (8.47 mmoles) of DCC were added. The mixture was stirred for twenty-four hours at 4° C. The resulting insoluble material was removed by filtration, and the filtrate was evaporated in vacuo. The resulting residue was re-dissolved in ethyl acetate, and the ethyl acetate was washed successively with 1 N aqueous sodium bicarbonate, water, cold 0.75 N citric acid, and water. The solution then was dried over magnesium sulfate and evaporated in vacuo. The residue was chromatographed on Grace and Davidson G-62 silica gel to give 4.1 g. (69%) of the title compound. $[\alpha]_D^{25} -13.1°$ (C=0.5, MeOH).

Analysis, calculated for $C_{34}H_{48}N_6O_8S$ (700.86): C, 58.27; H, 6.90; N, 11.99. Found: C, 58.05; H, 6.62; N, 11.73.

Amino acid analysis, found: Tyr, 1.00; Ala, 1.01; Gly, 0.99; Phe, 1.00; NH$_3$, 1.01.

E. L-Tyrosyl-D-alanyl-glycyl-L-phenylalanyl-N$^\alpha$-methyl-L-methionylamide acetate.

To 15 ml. of thioanisole were added 8.3 g. (0.012 mole) of the product from Part D. The mixture was cooled to 0° C., and 50 ml. of cold TFA were added. The mixture was stirred at 0° C. for 30 minutes and then was diluted with several volumes of ether. The resulting precipitate was collected and dried to give 8 g. of the crude trifluoroacetate salt. The salt was dissolved in a sufficient volume of an aqueous buffer containing 1% pyridine and 0.05% acetic acid to make 60 ml. The solution was applied to a 5×138 cm. column of DEAE Sephadex A-25 (acetate form) previously equilibrated with the same buffer. The UV absorbance at 280 mµ was monitored, and the product eluting between 1270 ml. and 1950 ml. was collected. The buffer was lyophilized. The residue was dissolved in about 200 ml. of 1 N acetic acid, and the solution was lyophilized. A final lyophilization from water-acetonitrile (3:1) gave 6.64 g. (83%) of the title compound. $[\alpha]_D^{25}$ +21.7 (C=1, 1 N HCl).

Analysis, calculated for $C_{31}H_{44}N_6O_8S$ (660.79): C, 56.35; H, 6.71; N, 12.72; O, 19.37. Found: C, 56.50; H, 6.46; N, 12.62; O, 19.25.

Amino acid analysis, found: Tyr, 1.00; Ala, 1.01; Gly, 1.00; Phe, 0.99; NH$_3$, 1.03.

The compounds of this invention are useful analgesics. The analgesic activity of the compounds of this invention is demonstrated by the mouse hot plate test. In this test, a mouse is placed inside an upright acrylic cylinder comprising, as its base, a hot plate surface which is maintained at 52° C. In this test, the mouse is given, by subcutaneous injection, a predetermined amount of test compound dissolved or suspended in a suitable carrier. A predetermined period subsequent to administration of the test compound is permitted to elapse, and the mouse then is placed on the hot plate surface. The latencies in seconds until the occurrence of each of two separate phenomena then are recorded. First, the latency until the mouse licks its hind paw is measured, and, secondly, the latency until the mouse jumps from the hot plate surface is measured. An agent which exhibits analgesic activity produces an increase in these latencies over those of control mice which receive injections only of the carrier. This must occur in a dose range which produces no motor incoordination or incapacitation. The following Tables record the results obtained from this test, comparing them with a control, with natural enkephalin, and with natural enkephalin converted to its amide. Table I provides latency to hind paw lick; Table II provides latency to escape jump; and Table III provides an indication of the percentage of animals in each test group which exhibited an analgesic effect. The criterion for an affirmative analgesic effect is as follows: the latency for the hind paw lick or escape jump for a treated animal must be equal to or greater than the mean control latency plus two standard deviations of the mean. Each result provided in the following Tables I and II represents mean value plus or minus standard error and Table III the percentage obtained from at least 9 mice and up to as many as 40 mice.

TABLE I

Analgesic Activity
Latency to Hind Paw Lick, Seconds

| Compound[c] | Time Elapse, min. | Control | Dose, mg/kg.[a] | | | | | |
|---|---|---|---|---|---|---|---|---|
| | | | 1 | 3 | 10 | 30 | 100 | 200 |
| Met$^5$-Enkephalin[b] | 5 | 29.5 ± 2.6 | — | — | — | — | 33.3 ± 2.2 | — |
| | 10 | 33.9 ± 4.5 | — | — | — | — | — | 30.1 ± 2.6 |
| Met$^5$-Enkephalin amide | 5 | 33.1 ± 1.1 | — | — | — | — | 33.6 ± 2.2 | 43.1 ± 2.9[1] |
| | 15 | 33.3 ± 0.8 | — | — | 35.0 ± 1.8 | 34.5 ± 2.2 | 28.6 ± 2.2 | 39.1 ± 3.7[1] |
| A | 5 | 33.1 ± 1.1 | — | 43.2 ± 3.2[1] | 48.9 ± 6.9[1] | 56.8 ± 9.7[1] | — | — |
| | 15 | 33.3 ± 0.8 | 30.3 ± 1.5 | 38.6 ± 2.2[1] | 40.6 ± 1.7[1] | 67.7 ± 9.3[1] | — | — |
| | 30 | 32.9 ± 1.8 | — | 34.5 ± 1.6 | 43.8 ± 2.3[1] | 48.7 ± 3.5[1] | — | — |
| B | 5 | 33.1 ± 1.1 | — | — | 37.4 ± 2.5[2] | 35.8 ± 3.5 | 46.3 ± 3.0[1] | — |
| | 15 | 33.3 ± 0.8 | — | — | 38.8 ± 2.3[1] | 35.1 ± 2.1 | — | — |
| | 30 | 32.9 ± 1.8 | — | — | — | 29.3 ± 2.1 | — | — |
| C | 15 | 33.3 ± 0.8 | 35.3 ± 2.7 | 32.8 ± 1.0 | 38.4 ± 1.9[1] | 40.6 ± 2.1[1] | — | — |
| D | 5 | 33.1 ± 1.1 | — | — | — | 37.6 ± 2.7 | — | — |
| | 15 | 33.3 ± 0.8 | 34.2 ± 2.2 | 39.9 ± 2.0[1] | 35.4 ± 2.8 | 37.4 ± 2.8[2] | — | — |
| | 30 | 32.9 ± 1.8 | — | — | — | 30.7 ± 2.8 | — | — |
| E | 5 | 33.1 ± 1.1 | — | — | — | 35.3 ± 2.9 | — | — |
| | 15 | 33.3 ± 0.8 | 31.0 ± 3.5 | 31.9 ± 2.5 | 36.8 ± 2.5 | 44.5 ± 3.1[1] | — | — |
| | 30 | 32.9 ± 1.8 | — | — | — | 30.2 ± 2.4 | — | — |
| F | 15 | 32.8 ± 2.9 | — | 43.7 ± 3.2[1] | — | — | — | — |
| | 15 | 35.7 ± 3.9 | — | — | 50.2 ± 5.3[1] | — | — | — |
| G | 15 | 30.0 ± 2.4 | 34.0 ± 2.4[e] | — | — | — | — | — |
| | 15 | 27.2 ± 2.2 | — | 34.7 ± 2.1[1] | 34.4 ± 1.4[1] | — | — | — |

TABLE II

Analgesic Activity
Latency to Escape Jump, Seconds

| Compound[c] | Time Elapse, min. | Control | Dose, mg./kg.[a] | | | | | |
|---|---|---|---|---|---|---|---|---|
| | | | 1 | 3 | 10 | 30 | 100 | 200 |
| Met[5]-Enkephalin[b] | 5 | 79.5 ± 9.6 | — | — | — | — | 82.2 ± 5.2 | — |
| | 10 | 64.2 ± 10.4 | — | — | — | — | — | 92.8 ± 8.9[2] |
| Met[5]-Enkephalin amide | 5 | 70.8 ± 4.7 | — | — | — | — | 95.6 ± 10.6[1] | 96.8 ± 7.7[1] |
| | 15 | 73.0 ± 2.4 | — | — | 77.3 ± 6.8 | 82.8 ± 9.1 | 103.6 ± 10.4[1] | 105.8 ± 10.4[1] |
| A | 5 | 70.8 ± 4.7 | — | 140.4 ± 14.5[1] | 165.3 ± 20.2[1] | 194.8 ± 22.1[1] | — | — |
| | 15 | 73.0 ± 2.4 | 96.7 ± 8.0[1] | 131.3 ± 7.9[1] | 157.6 ± 7.0[1] | 214.3 ± 7.5[1] | — | — |
| | 30 | 92.4 ± 7.0 | — | 83.6 ± 6.5 | 109.4 ± 7.1 | 143.0 ± 8.8[1] | — | — |
| B | 5 | 70.8 ± 4.7 | — | — | 118.5 ± 11.2[1] | 125.0 ± 14.0[1] | 163.9 ± 12.0[1] | — |
| | 15 | 73.0 ± 2.4 | — | — | 92.4 ± 8.2[1] | 113.3 ± 6.1[1] | — | — |
| | 30 | 92.4 ± 7.0 | — | — | — | 84.8 ± 11.6 | — | — |
| C | 15 | 73.0 ± 2.4 | 89.2 ± 20.0 | 113.7 ± 7.2[1] | 121.2 ± 13.1[1] | 162.3 ± 19.1[1] | — | — |
| D | 5 | 70.8 ± 4.7 | — | — | — | 80.2 ± 14.3 | — | — |
| | 15 | 73.0 ± 2.4 | 88.7 ± 6.8 | 102.8 ± 9.5[1] | 107.0 ± 12.3[1] | 115.6 ± 13.9[1] | — | — |
| | 30 | 92.4 ± 7.0 | — | — | — | 70.8 ± 4.4[2] | — | — |
| E | 5 | 70.8 ± 4.7 | — | — | — | 97.7 ± 14.3[2] | — | — |
| | 15 | 73.0 ± 2.4 | 79.9 ± 12.1 | 103.1 ± 12.4[1] | 116.4 ± 9.6[1] | 158.1 ± 13.7[1] | — | — |
| | 30 | 92.4 ± 7.0 | — | — | — | 63.2 ± 8.9[2] | — | — |
| F | 15 | 75.6 ± 9.9 | — | 182.4 ± 21.3[1] | — | — | — | — |
| | 15 | 57.3 ± 6.0 | — | — | 215.8 ± 12.8[1] | — | — | — |
| G | 15 | 72.3 ± 8.5 | 130.5 ± 12.5[1][e] | — | — | — | — | — |
| | 15 | 53.8 ± 6.7 | — | 128.2 ± 20.4[1] | 159.9 ± 22.7[1] | — | — | — |

TABLE III

Analgesic Activity
Animals Showing Analgesic Response, Percent

| Compound[c] | Time Elapse, min. | Dose, mg./kg.[a,d] | | | | | | | | | | | |
|---|---|---|---|---|---|---|---|---|---|---|---|---|---|
| | | 1 | | 3 | | 10 | | 30 | | 100 | | 200 | |
| | | HPL | EJ | HPL | EJ | HPL | EJ | HPL | EJ | HPL | EJ | HPL | EJ |
| Met[5]-Enkephalin[b] | 5 | — | — | — | — | — | — | — | — | 0 | 0 | — | — |
| | 10 | — | — | — | — | — | — | — | — | — | — | 11 | 22 |
| Met[5]-Enkephalin amide | 5 | — | — | — | — | — | — | — | — | 12 | 24 | 38 | 19 |
| | 15 | — | — | — | — | 14 | 0 | 28 | 13 | 13 | 24 | 31 | 25 |
| A | 5 | — | — | 40 | 60 | 50 | 80 | 60 | 80 | — | — | — | — |
| | 15 | 5 | 21 | 28 | 55 | 40 | 82 | 85 | 100 | — | — | — | — |
| | 30 | — | — | 10 | 10 | 53 | 50 | 57 | 67 | — | — | — | — |
| B | 5 | — | — | — | — | 25 | 50 | 19 | 50 | 50 | 81 | — | — |
| | 15 | — | — | — | — | 35 | 21 | 20 | 40 | — | — | — | — |
| | 30 | — | — | — | — | — | — | 0 | 20 | — | — | — | — |
| C | 15 | 11 | 11 | 0 | 50 | 25 | 38 | 33 | 89 | — | — | — | — |
| D | 5 | — | — | — | — | — | — | 13 | 22 | — | — | — | — |
| | 15 | 11 | 0 | 31 | 25 | 22 | 22 | 25 | 33 | — | — | — | — |
| | 30 | — | — | — | — | — | — | 11 | 0 | — | — | — | — |
| E | 5 | — | — | — | — | — | — | 22 | 33 | — | — | — | — |
| | 15 | 11 | 11 | 6 | 31 | 31 | 56 | 44 | 78 | — | — | — | — |
| | 30 | — | — | — | — | — | — | 11 | 0 | — | — | — | — |
| F | 15 | — | — | 30 | 70 | 40 | 100 | — | — | — | — | — | — |
| G | 15 | 10 | 30[e] | 44 | 60 | 10 | 70 | — | — | — | — | — | — |

Footnotes

[a]Unless otherwise indicated, tests were run using saline control. The numerals "1" and "2" appearing as superscripts indicate that the result is significant to $P < 0.01$ and to $P < 0.05$, respectively.

[b]Test and control run in acacia with compound present as suspension.

[c]The designations refer to the following compounds:

A L-Tyrosyl-D-alanyl-glycyl-L-phenylalanyl-$N^\alpha$-methyl-L-methionylamide hydrochloride.
B L-Tyrosyl-D-alanyl-glycyl-L-phenylalanyl-L-methionylamide hydrochloride.
C L-Tyrosyl-D-alanyl-L-alanyl-L-phenylalanyl-$N^\alpha$-methyl-L-methionylamide 1.25 hydrochloride monoacetate.
D L-Tyrosyl-D-leucyl-glycyl-L-phenylalanyl-$N^\alpha$-methyl-L-methionylamide sesquihydrochloride monoacetate.
E L-Tyrosyl-D-alanyl-glycyl-$N^\alpha$-methyl-L-phenylalanyl-$N^\alpha$-methyl-L-methionylamide hydrochloride trihydrate.
F L-Tyrosyl-D-alanyl-glycyl-L-phenylalanyl-$N^\alpha$-methyl-L-leucylamide acetate.
G L-Tyrosyl-D-alanyl-glycyl-L-phenylalanyl-L-$N^\alpha$methyl-S-ethyl-cysteinylamide acetate.

[d]HPL = hind paw lick. EJ = escape jump.

[e]When tested at 0.3 mg./kg., latency to hind paw lick was 33.9 ± 2.3 seconds, latency to escape jump was 129.0 ± 11.5 seconds, and analgesic response was 10% for HPL and 60% for EJ.

We claim:

1. A compound of the formula

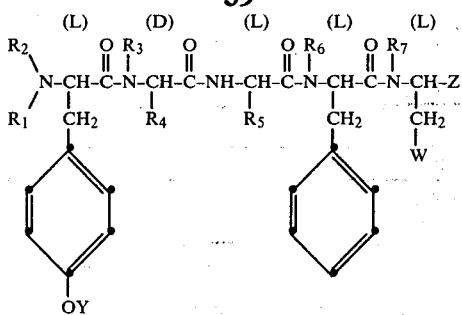

and pharmaceutically acceptable non-toxic acid addition salts thereof, in which:

L and D, when applicable, define the chirality;

$R_1$ is hydrogen, $C_1$-$C_3$ primary alkyl, or allyl;

$R_2$ is hydrogen or $C_1$-$C_3$ primary alkyl, subject to the limitation that when $R_1$ is allyl, $R_2$ is hydrogen;

$R_3$ is hydrogen or $C_1$-$C_3$ primary alkyl;

$R_4$ is $C_1$-$C_4$ primary or secondary alkyl;

$R_5$ is hydrogen or $C_1$-$C_4$ primary or secondary alkyl;

$R_6$ is hydrogen or $C_1$-$C_3$ primary alkyl;

$R_7$ is $C_1$-$C_3$ primary alkyl;

Y is hydrogen or acetyl;

Z is

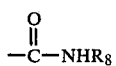

in which $R_8$ is $C_1$-$C_3$ alkyl or hydrogen; and W is isopropyl, —$VR_9$, or —$CH_2$—X—$CH_3$, in which V is O or S, $R_9$ is $C_1$-$C_4$ alkyl or aralkyl, and X is O, S, or —$CH_2$—.

2. Compound of claim 1, in which Y is hydrogen.
3. Compound of claim 1, in which $R_1$ and $R_2$ are hydrogen.
4. Compound of claim 1, in which $R_1$ is allyl.
5. Compound of claim 1, in which $R_3$ is hydrogen.
6. Compound of claim 1, in which $R_4$ is methyl.
7. Compound of claim 1, in which $R_5$ is hydrogen.
8. Compound of claim 1, in which $R_6$ is hydrogen.
9. Compound of claim 1, in which W is —$CH_2$—X—$CH_3$.
10. Compound of claim 9, in which Y is hydrogen.
11. Compound of claim 9, in which $R_1$ and $R_2$ are hydrogen.
12. Compound of claim 9, in which $R_1$ is allyl.
13. Compound of claim 9, in which $R_3$ is hydrogen.
14. Compound of claim 9, in which $R_4$ is methyl.
15. Compound of claim 9, in which $R_5$ is hydrogen.
16. Compound of claim 9, in which $R_6$ is hydrogen.
17. Compound of claim 9, in which X is sulfur.
18. Compound of claim 9, in which $R_7$ is methyl.
19. Compound of claim 9, in which $R_8$ is hydrogen.
20. Compound of claim 1, in which $R_7$ is methyl.
21. Compound of claim 18, in which $R_8$ is hydrogen.
22. Compound of claim 21, in which $R_6$ is hydrogen.
23. Compound of claim 22, in which X is sulfur.
24. Compound of claim 23, in which Y is hydrogen.
25. Compound of claim 24, in which $R_3$ is hydrogen.
26. Compound of claim 25, in which $R_1$ and $R_2$ are hydrogen.
27. Compound of claim 26, in which $R_5$ is hydrogen.
28. Compound of claim 27, in which $R_4$ is methyl.
29. Compound of claim 27, in which $R_4$ is isobutyl.
30. Compound of claim 26, in which $R_5$ is methyl.
31. Compound of claim 30, in which $R_4$ is methyl.
32. Compound of claim 21, in which $R_1$, $R_2$, $R_3$, $R_5$, and Y each are hydrogen; $R_4$ and $R_6$ are methyl; and X is sulfur.
33. Compound of claim 1 in which W is isopropyl.
34. Compound of claim 33, in which Y is hydrogen.
35. Compound of claim 33, in which $R_1$ and $R_2$ are hydrogen.
36. Compound of claim 33, in which $R_1$ is allyl.
37. Compound of claim 33, in which $R_3$ is hydrogen.
38. Compound of claim 33, in which $R_4$ is methyl.
39. Compound of claim 33, in which $R_5$ is hydrogen.
40. Compound of claim 33, in which $R_6$ is hydrogen.
41. Compound of claim 33, in which $R_7$ is methyl.
42. Compound of claim 41, in which $R_8$ is hydrogen.
43. Compound of claim 42, in which $R_6$ is hydrogen.
44. Compound of claim 43, in which Y is hydrogen.
45. Compound of claim 44, in which $R_3$ is hydrogen.
46. Compound of claim 45, in which $R_1$ and $R_2$ are hydrogen.
47. Compound of claim 46, in which $R_5$ is hydrogen.
48. Compound of claim 47, in which $R_4$ is methyl.
49. Compound of claim 1, in which W is —$VR_9$.
50. Compound of claim 49, in which V is sulfur.
51. Compound of claim 50, in which Y is hydrogen.
52. Compound of claim 50, in which $R_1$ and $R_2$ are hydrogen.
53. Compound of claim 50, in which $R_3$ is hydrogen.
54. Compound of claim 50, in which $R_4$ is methyl.
55. Compound of claim 50, in which $R_5$ is hydrogen.
56. Compound of claim 50, in which $R_6$ is hydrogen.
57. Compound of claim 50, in which $R_8$ is hydrogen.
58. Compound of claim 57, in which $R_9$ is ethyl or p-methoxybenzyl.
59. Compound of claim 58, in which $R_7$ is methyl.
60. Compound of claim 59, in which $R_6$ is hydrogen.
61. Compound of claim 60, in which Y is hydrogen.
62. Compound of claim 61, in which $R_3$ is hydrogen.
63. Compound of claim 62, in which $R_1$ and $R_2$ are hydrogen.
64. Compound of claim 63, in which $R_5$ is hydrogen.
65. Compound of claim 64, in which $R_4$ is methyl.
66. Compound of claim 65, in which $R_9$ is ethyl.
67. Compound of claim 65, in which $R_9$ is p-methoxybenzyl.

* * * * *